(12) United States Patent
Smits et al.

(10) Patent No.: US 7,057,033 B2
(45) Date of Patent: Jun. 6, 2006

(54) FRACTIONATED POLYDISPERSE COMPOSITIONS

(75) Inventors: Georges Smits, Gijzegem-Aalst (BE); Luc Daenekindt, Gijzegem-Aalst (BE); Karl Booten, Geetbets (BE)

(73) Assignee: Tiense Suikerrafinaderij N.V. (BE)

( * ) Notice: Subject to any disclaimer, the term of this patent is extended or adjusted under 35 U.S.C. 154(b) by 159 days.

(21) Appl. No.: 09/943,574

(22) Filed: Aug. 30, 2001

(65) Prior Publication Data

US 2002/0028928 A1 Mar. 7, 2002

Related U.S. Application Data

(63) Continuation of application No. 08/765,874, filed on May 27, 1997, now Pat. No. 6,303,778.

(51) Int. Cl.
*C07H 1/08* (2006.01)

(52) U.S. Cl. ............... 536/128; 536/123; 536/124; 536/127; 514/54

(58) Field of Classification Search ............... 536/128, 536/123, 124, 127, 123.12; 514/54
See application file for complete search history.

(56) References Cited

U.S. PATENT DOCUMENTS

| | | | |
|---|---|---|---|
| 1,970,871 A | | 8/1934 | Tate et al. ............ 127/34 |
| 1,971,871 A | | 8/1934 | Paine et al. ............ 127/34 |
| 2,555,356 A | | 6/1951 | Marchand ............ 127/34 |
| 4,285,735 A | | 8/1981 | Mitchell et al. |
| 5,478,732 A | * | 12/1995 | Kunz et al. ............ 435/101 |
| 6,303,778 B1 | * | 10/2001 | Smits et al. ............ 536/128 |

FOREIGN PATENT DOCUMENTS

| | | |
|---|---|---|
| EP | 0 532 775 A1 | 3/1993 |
| SU | 487118 | 2/1976 |
| WO | 8702679 | 5/1987 |
| WO | 87/02679 | 5/1987 |
| WO | 9213005 | 8/1992 |
| WO | WO 93/06744 | 4/1993 |
| WO | 9412541 | 6/1994 |

OTHER PUBLICATIONS

"Application of Gel Permeation Chromatograhic Systems to the Determination of the Molecular Weight of Inulin" Journal of Chromatography 348, 1985, pp. 187–197.
"Zur Polymorphic Hochmolekularer Ststanzen" Katz et al., Rec. Trav. Chim. 50, 1133–1137, 1931.
Solubility of Inulin: Yanovsky et al., J. Amer. Chem. Soc. 55, 3658–3663, 1933.
"The Ployfuctosans and Difuretose Anhydrides" Adv. Carbohydrates Chemistry, 2, pp. 253–277, 1946.
"Crystallization" Perry et al., Chemical Engineers' Handbook, 5th Edition, 17–8 to 17–18, 1973.

* cited by examiner

*Primary Examiner*—James O. Wilson
*Assistant Examiner*—Howard V. Owens
(74) *Attorney, Agent, or Firm*—Hayes Soloway P.C.

(57) ABSTRACT

The present invention concerns a new fractionated polydisperse carbohydrate composition having the following definition: an av. DP which is significantly higher than the av. DP of a native polydisperse carbohydrate composition, significantly free of low molecular monomers, dimmers, and oligomers, significantly free of impurities chosen among the group consisting of colourings, salts, proteins and organic acids, significantly free of technological aids such as solubility affecting products. The present invention concerns also the preparation process of the composition according to the invention.

25 Claims, 16 Drawing Sheets

FIG. 3

| g‰ SUGARS | |
|---|---|
| fructose | 0.00 |
| glucose | 0.00 |
| DFA | 0.00 |
| saccharose | 0.00 |
| F2 | 0.00 |
| GF2 | 0.00 |
| F3 | 0.00 |
| GF3 | 0.00 |
| F4 | 0.00 |
| GF4 | 0.13 |
| F5 | 0.00 |
| GF5 | 0.13 |
| F6 | 0.00 |
| GF6 | 0.16 |
| F7 | 0.00 |
| GF7 | 0.19 |
| F8 | 0.00 |
| GF8 | 0.31 |
| F9 | 0.00 |
| DP10 | 0.25 |
| > DP10 | 98.84 |
| Σ | 100.00 |

GF8=GF8+F9

| g/100g. sugar | Raftiline ST | filtercake | filtercake after washing | filtrate + washwater |
|---|---|---|---|---|
| fructose | 0.93 | 1.08 | 0.00 | 2.8 |
| glucose | 0.25 | 0.21 | 0.00 | 0.5 |
| DP2 | 0.00 | 0.00 | 0.00 | 0 |
| Saccharose | 5.63 | 2.81 | 0.03 | 8.2 |
| F3 | 0.17 | 0.00 | 0.00 | 0.4 |
| DP3 | 2.81 | 1.68 | 0.08 | 5.1 |
| DP4 | 3.13 | 2.02 | 0.16 | 5.5 |
| DP5+ | 87.09 | 92.21 | 99.73 | 77.5 |
| FOS | 93.2 | 95.91 | 99.7 | 88.5 |
| DP | 12.3 | 17.5 | 25.8 | 9.5 |
| %DS | - | 49.7% | 41.9% | - |
| return (yield) | - | 44% | 35% | - |

|  | Raw inulin | filtercake | filtercake after washing |
|---|---|---|---|
| fructose (g%g sugar) | 0 | 0,26 | 0 |
| glucose (g%g sugar) | 0 | 0 | 0 |
| other DP2 (g%g sugars) | 0 | 0 | 0 |
| saccharose (g%g sugar) | 7,87 | 3,06 | 0 |
| F3 (g%g sugar) | 0 | 0 | 0 |
| DP3 (g%g sugar) | 4,27 | 1,7 | 0 |
| DP4 (g%g sugar) | 5,09 | 2,15 | 0 |
| DP5+ (g%g sugar) | 82,8 | 92,8 | 100 |
| FOS. g%g sugar) | 92,1 | 96,7 | 100 |
| DP | 9,2 | 14,6 | 20 |
| %DS | 16,69 | 59,39 | 43,49 |
| return (yield) | - | 48,00% | 33,00% |
| conductivity (ms) | 10,1 | 4,9 | 0,126 |
| ashcontent | 6,06% | 2,94% | 0,08% |

FIG 15

FRACTIONATED POLYDISPERSE COMPOSITIONS

This is a continuation of application Ser. No. 08/765,874, filed May 27, 1997, now U.S. Pat. No. 6,303,778.

The invention relates to new fractionated polydisperse carbohydrate compositions, more particularly new fractionated fructan compositions and more specifically to new fractionated inulin compositions, and also to the products in which these compositions are incorporated. The invention also relates to a preparation process for the fractionation of the polydisperse compositions.

BACKGROUND TO THE INVENTION

Our present modern way of life imposes more and more demands on products used for food, feed and pharmaceutical purposes, body care, etc. In this context, there is a continuous need for products which have reduced calorific values, have a low fat content, have an increased fibre content, have a beneficial effect on intestinal and cutageneous microflora, have a lower sugar content, do not cause dental caries, possess physiologically functional characteristics.

It is known that various carbohydrates, including fructans such as inulin, can fulfill these demands and can therefore be valuable ingredients for food products, functional food or feed, OTC and pharmaceutical products, cosmetic products etc.

It is known e.g. native inulin can be obtained by industrial methods (F. Perschak, Zükerind.115, (1990), p.466). Through hot water extraction, an inulin-containing containing extract is separated out from tuber or root cuttings taken from inulin-containing plants. This extract is then demineralised and decolorized. Raftiline® ST is a commercially available product which contains native chicory inulin (Tiense Suikerraffinaderij, Belgium).

These inulin extracts are in fact a mixture of polymer molecules of various chain lengths.

A polydisperse carbohydrate composition such as e.g. inulin can be characterised by the chain length of the individual molecules (the degree of polymerisation or DP), and also by the percentage distribution of the number of molecules of a particular chain length, as well as by the average degree of polymerisation (av. DP).

A native polydisperse composition retains the molecular structure and the polydispersity pattern of the product as separated from its original source.

The degree of polymerisation of native chicory inulin molecules is between 2 and 60, the av. DP is around 11. The percentage distribution of he molecule fractions is approximately 31% for DP 2–9, 24% for DP 10–20, 28% for DP 21–40 and 17% for DP>40 respectively. Native inulin from dahlias with an av. DP of 20 contains a significantly smaller share of oligofructoses and double the quantity of molecules with a chain length of DP>40. Native Jerusalem artichoke inulin on the other hand contains extremely few molecules with DP>40, only about 6%. The oligomer fraction DP<10 accounts for approximately half of the molecules of the native polydisperse inulin of Jerusalem artichoke.

The polydispersity pattern of e.g. fructans strongly depends not only on the original production source from which the fructans are obtained (e.g. in vivo synthesis with plants or microorganisms or in vitro synthesis with enzymes), but also on the point of time at which the polydisperse compositions are extracted (e.g. plant harvest time, the action time of enzymes, etc.). The manner in which the polydisperse compositions are extracted likewise plays a role.

In addition, extracted native polydisperse compositions frequently contain a significant amount of other products such as e.g. monosaccharides and disaccharides such as glucose, fructose and saccharose and impurities such as proteins, salts, colourings, organic acids and technical aids such as solubility affecting products.

State of the Technology

Known products with a changed DP are:

gamma inulin with molecules that have a very specific DP between 50 and 63, as described in WO 87/02679;

inulin I 2255, I 3754 and I 2880 which have an av. DP which is significantly higher than the av. DP of the native inulin from which they are prepared, respectively native chicory, dahlia and Jerusalem artichoke (Sigma, USP.) and which are non-food graded.

fibruline LC (Warcoing, Belgium) a chicory inulin with an av. DP not appreciably higher than native chicory inulin and which contains a significant amount of impurities and low molecular carbohydrates, making its use in many applications impossible.

A number of processes are known to exist and allow e.g. the production of fractionated inulin with a higher av. DP.

Using alcohol based solvents such as methanol, ethanol or isopropanol, inulin with a higher av. DP can be precipitated and separated by centrifugation. However, this is a fairly complex method. The precipitation is often combined with extremely low temperatures (4° C. and low initial inulin concentration). The alcohol must be removed and the volume that needs to be reconcentrated is large. The yield of this process is extremely low, notwithstanding the fact that a relatively pure end product is obtained.

It is also known that aqueous solutions of inulin can be subjected to crystallisation by the addition of grafting crystals in such a way that the longer chains precipitate and can be separated out by centrifugation.

E. Berghofer (Inulin and Inulin containing crops, Ed. A. Fuchs, Elsevers Sc. Publ., (1993), p 77) describes the isolation of inulin from chicory by means of crystallisation with a slow pattern of cooling (3° C./hour from 95° C. to 4° C.). In this way it is only possible to separate out small amounts of inulin and the product obtained is not sufficiently pure.

It is known (Le Sillon Belge, Apr. 24, 1989) that inulin can be divided into various polymer fractions by applying the technique used in classical industrial physical chemistry, i.e. separation through fractional crystallisation. For this, an inulin solution is gradually cooled using ceiling temperatures between 40° C. and 10° C., where necessary making use of grafting crystals. It is usual for the molecules with a higher DP to precipitate first, followed by the shorter ones, since molecules with a higher DP are less soluble. The isolated fractions then still need to be separated through centrifugation or filtration and washed.

By using enzyme synthesis and a native inulin, or sucrose solution, molecules with a high DP can be obtained (EP 532,775). Though the end product is practically free of oligomers, the remaining sucrose and fructose must be removed using supplementary methods.

As described in EP 627490, it is possible by the use of inulinase to break down the low DP fraction in native inulin. The percentage distribution of the number of molecules with a low DP will be diminished in such a way that the av. DP of the polydisperse end product will increase. The breakdown products glucose and fructose will need to be removed using supplementary methods.

U.S. Pat. No. 4,285,735 describes a preparation process of a dahlia inulin that contains minor amount of inulides, proteins, colours, flavours, external bodies and minerals.

JP-03/280856 describes a production process of an aqueous paste shaped composition comprising β-(2->1) fructan with a degree of polymerisation of 10 to 100. The said fructan is dispersed and present in the paste as a fine granular material.

Aims of the Invention

Notwithstanding the fact that a number of preparation processes of a fractionated fructan composition such as inulin are known, down to the present time there has been no fractionated polydisperse inulin (i.e. inulin with a changed av. DP) available which results in an end product combining four important characteristics in a single product, i.e.

an average DP which is significantly higher than the average DP of native inulin;

an inulin composition which is significantly free of low molecular monosaccharides, dissaccharides and oligosaccharides; and a refined fractionated inulin which is significantly free of impurities such as colourings, salts, proteins and organic acids; and an end product which is free of technological aids such as solubility affecting products.

It may on the one hand be necessary to remove monosaccharides and dissaccharides and often also oligomer molecules from native polydisperse carbohydrate compositions since these are experienced as hindrances in certain applications. This problem has already been recognised and solved by the present patent application WO 94/12541. Raftiline® LS from Tiense Suikerraffinaderij in Belgium is a product which typically contains no or very few saccharides of a low molecular weight and which is prepared in accordance with WO 94/12541.

On the other hand it can be worthwhile to have available a particular polymer fraction of a polydisperse carbohydrate composition since this may more definitely demonstrate a specific characteristic of the native mixture or because new characteristics can be ascribed to the particular fraction.

The better the fractionation, the purer the end product prepared, the lower the polydispersity and the smaller the standard deviation from the av. DP.

It is therefore still desirable to prepare polydisperse carbohydrate compositions whose DP has been changed in respect to the av. DP of the polydisperse composition that served as starting product. Compositions such as these are referred to below as fractionated carbohydrate polydisperse compositions.

More specifically, the availability of a fractionated inulin composition pure enough to allow the preparation of a high performance inulin would permit many new developments both in the food sector and in other sectors. The availability of pure fractionated inulin also makes possible improvements to the known applications for inulin, if only for the reason that the same characteristics can be achieved using a significantly smaller amount of high performance inulin as compared to native inulin, where the share of low molecular products is decisive. All of which benefits the consumer. The facility of being able to provide inulin in fractions with a specific av. DP would likewise make it possible to develop new applications for inulin.

More generally, there remains the task of finding a new preparation process which allows carbohydrate molecules with a high DP to be fractionated from native polydisperse compositions on the understanding that an endeavour must be made to arrive at an industrially applicable, in other words profitable, methodology, permitting the production of large quantities.

During its research work into pure fractionated polydisperse carbohydrate compositions the applicant chose for crystallisation. Specifically, the known crystallisation methods for inulin were tried out, the aim being to achieve a pure separation of inulin molecules with a high DP. At that point the applicant came up against a filtration problem whenever it wished to use the known processes. When the attempt was made to precipitate chicory inulin according to the state of the art and afterwards to filter it, the filters became clogged, and when centrifugation was tried out, non pure fructans were obtained.

Furthermore the high DP molecule fraction continued to contain a significant amount of glucose, fructose, saccharose and oligomers. It was proved difficult to wash out the filter cake with hot or cold water and to remove these sugars and other non-carbohydrates using a simplified method, i.e. washing.

SUMMARY OF THE INVENTION

The present invention is related to a new fractionated polydisperse carbohydrate composition which responds to the following definition:

an av. DP which is significantly higher than the av. DP of the native polydisperse carbohydrate composition;

significantly free from low molecular monomers, diomers and oligomers;

significantly free of impurities chosen among the group consisting of colourings, salts, proteins and organic acids;

significantly free of technological aids, such as solubility affecting products.

Advantageously, said composition is a fractionated polydisperse fructan composition, preferably a composition with mainly β-linkages between the carbohydrate units.

Fructans are polydisperse compositions of carbohydrate where fructosyl-fructose linkages are predominant.

More specifically, the new fractionated fructan compositions are fractionated inulin compositions. Inulin has mainly β-D-(2->1) fructosyl-fructose linkages between the carbohydrate units. Most inulin molecules have a supplementary glucose unit on the non-reducing end of the inulin chain and a small number of molecules are branched. (L. De Leenheer, Starch/Stärke 46, (1994), p 193).

Preferably, the composition according to the invention is a fractionated polydisperse chicory inulin composition.

According to a preferred embodiment of the present invention, said composition is a solid form of a fractionated polydisperse inulin: "delta inulin", with a modified av. DP and in the form of spherical particles having the following characteristics:

diameter comprised between 1 and 100 μm, preferably between 5 and 70 μm, more preferably between 6 and 60 μm, radial symmetry, double breaking and perpendicular fade cross under polarised light.

More particularly, the invention relates to a high performance inulin, being said fractionated polydisperse inulin composition in a spray-dried form.

The invention also embraces the compositions in which these new fractionated polydisperse carbohydrate compositions according to the invention are incorporated, more particularly those products in which fractionated polydisperse fructans are used and more specifically those in which fractionated polydisperse inulin is used. The invention also includes those products which are produced by chemical or enzymatic modification of the new fractionated polydisperse carbohydrate compositions in accordance with the invention.

Preferably, in said modified compositions, the carbohydrates are etherified, esterified and/or oxidised.

The present invention concerns also a composition having a creamy structure comprising the fractionated polydisperse carbohydrate composition according to the invention and the pharmaceutical, cosmetical, feed and/or food compositions comprising the compositions according to the invention.

Said fractionated polydisperse carbohydrate composition may be also used in various fields, such as plastic formulations, plastic packaging, paper production, in textile industry, in ceramics, powder and metal production, in the dental sector, in electronics, bioelectronics, in batteries, automotive, adhesives and tobacco production, in waste treatment, in petroleum extraction, in production of paints, inks, coatings and detergents, in the production of diagnostic devices, culture mediums for microorganisms, . . . .

Another aspect of the present invention concerns a directed crystallisation process for a solution of a polydisperse carbohydrate composition which comprises a rapid achievement of a high degree of super saturation, obtained by a rapid cooling down involving an important temperature modification, by a rapid concentration increase involving an important concentration modification, or by a combination thereof.

The present invention is also related to a preparation process of the composition according to the invention, comprising the following steps:

the preparation of a metastable solution of a native polydisperse carbohydrate composition, a directed crystallisation of said metastable solution, a separation of the particles obtained after the crystallisation, a washing of the separated particles, possibly a drying of the washed particles, possibly a chemical or enzymatic treatment of the carbohydrates.

SHORT DESCRIPTION OF THE FIGURES

FIG. 3 shows a gas chromatographic analysis of high performance Raftiline® expressed in g/100 g carbohydrate.

Figure 11:
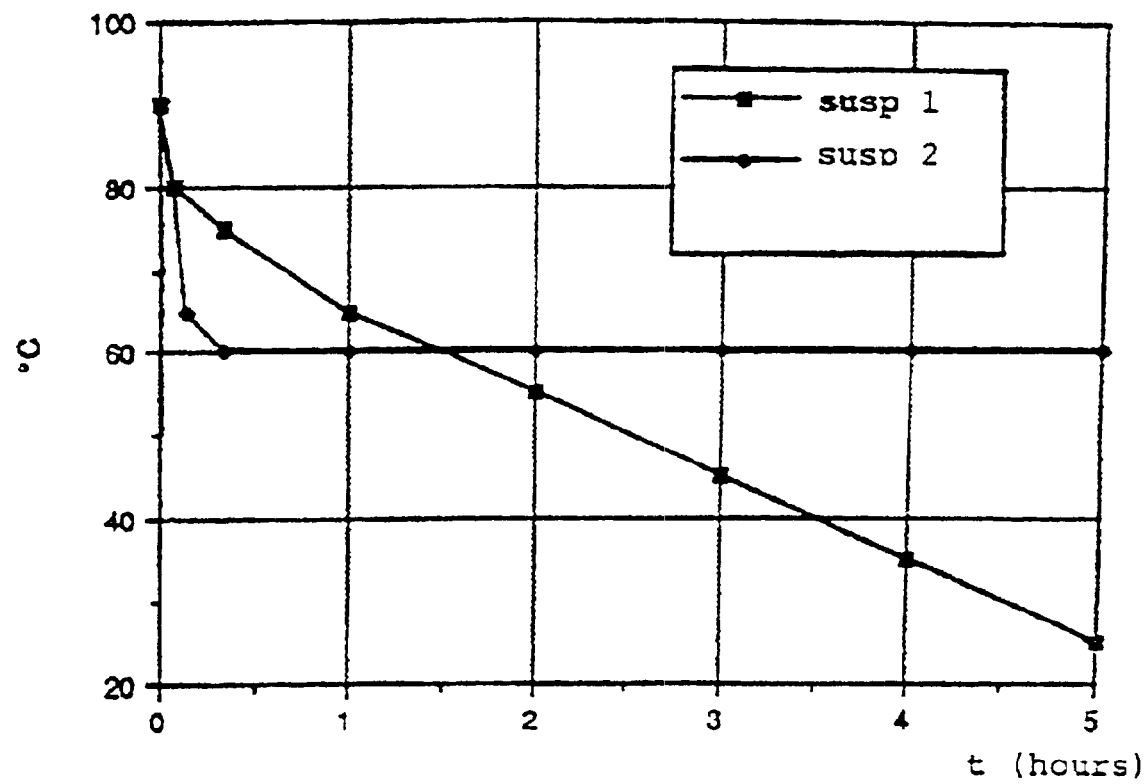

FIG. 11 shows a cooling down profile (temperature as function of time) for inulin solutions. Suspension 1 is undergoing a slow cooling down profile (example 2). Suspension 2 remains at a constant temperature of 60° C. (example 1).

Figure 12:
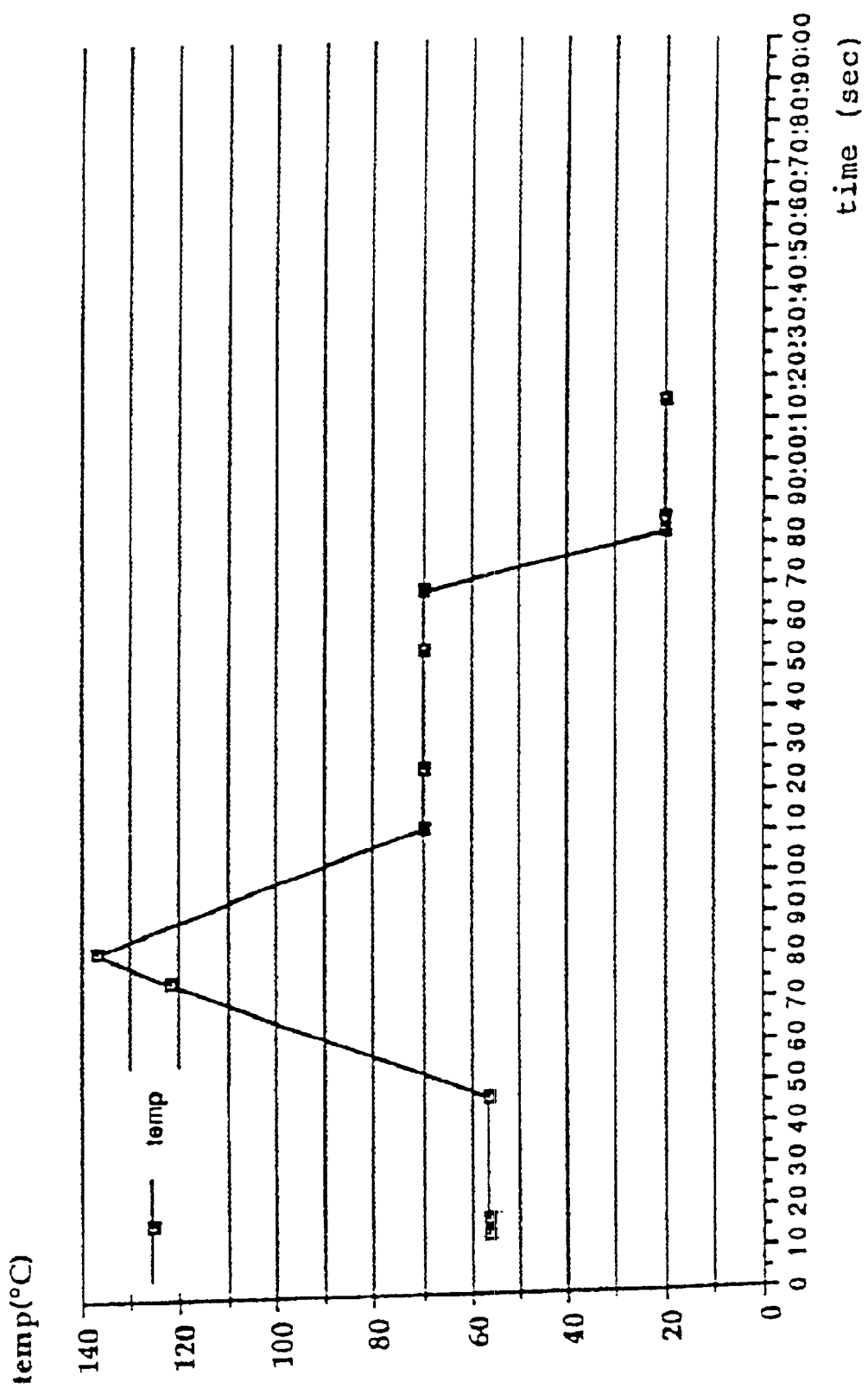

FIG. 12 shows a temperature profile (temperature as function of time) for the preparation of delta inulin (example 3).

Figures 13, 14:
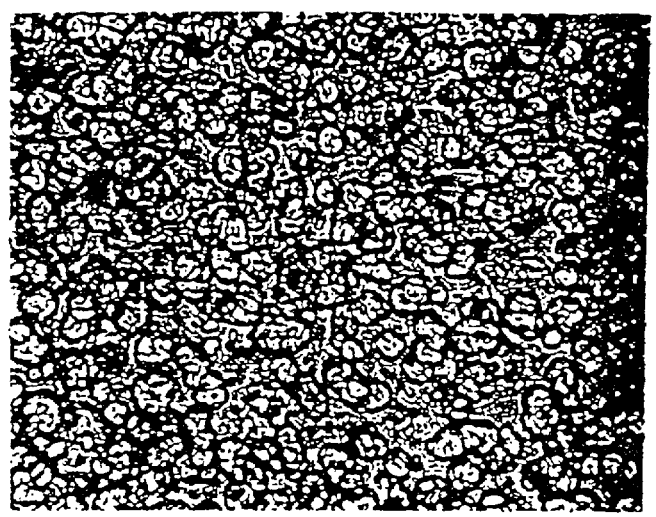

FIG. 13 shows the carbohydrate composition, DP, % DM and yield of Raftiline® ST, filter cake and filter cake after washing (example 3).

FIG. 14 is a photo (magnification×200) of delta inulin produced by a rapid cooling down profile. The particles are uniform and have a diameter of 25 µm (example 3).

FIG. 15 shows a carbohydrate composition, DP, % DM, yield, conductivity and ash content of the raw inulin staring product, filter cake and filter cake after washing.

Figure 16:
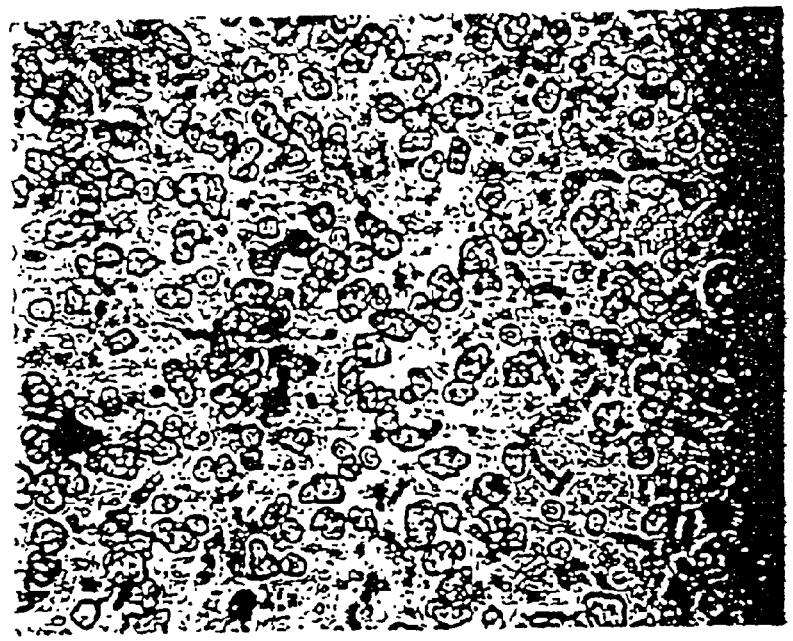

FIG. 16 is a photo (magnification×200) of delta inulin produced by a rapid cooling down profile without grafting (example 6)

Figure 17:
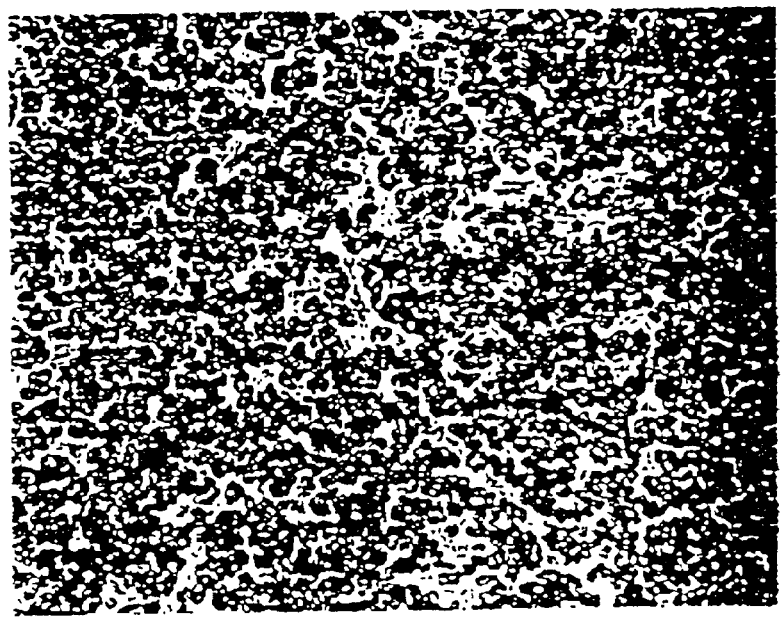

FIG. 17 is a photo (magnification×200) of delta inulin produced by a rapid cooling down profile with grafting (example 6).

Figure 18:
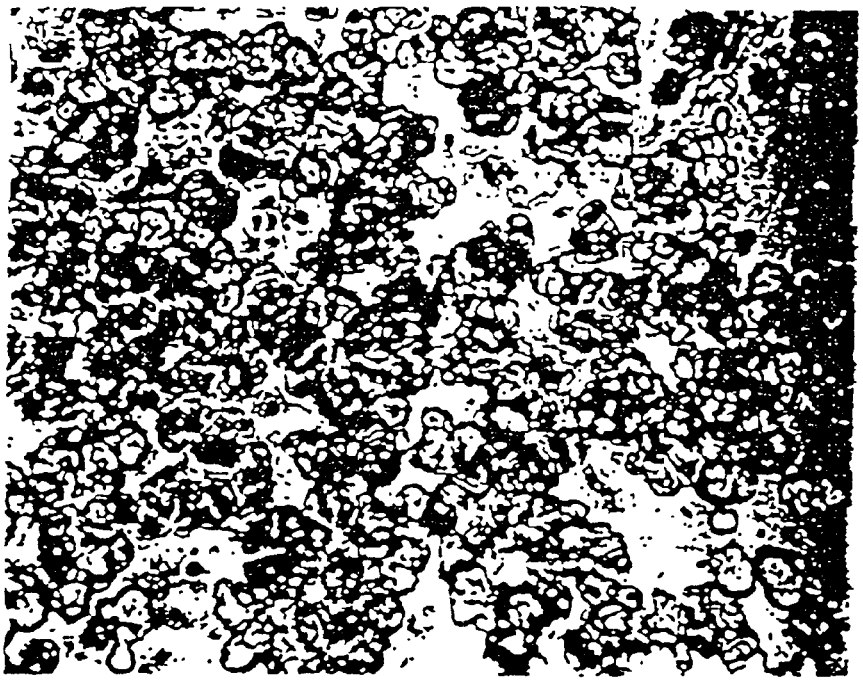

FIG. 18 is a photo (magnification×200) of delta inulin produced by a rapid cooling down profile without stirring (example 7).

Figure 19:
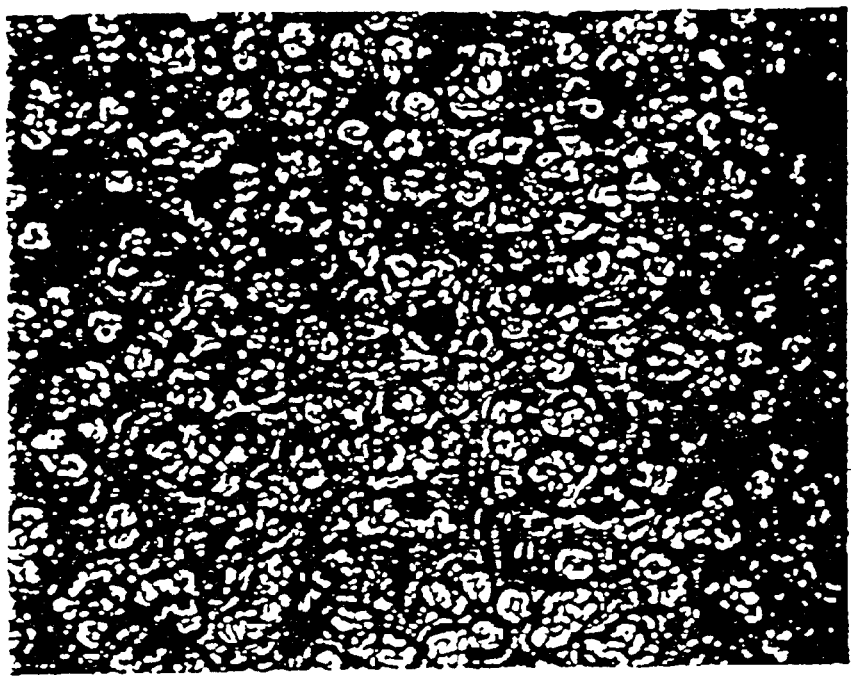

FIG. 19 is a photo (magnification×200) of delta inulin produced by a rapid cooling down profile and stirring at 20 t/min (example 7).

Figure 20:
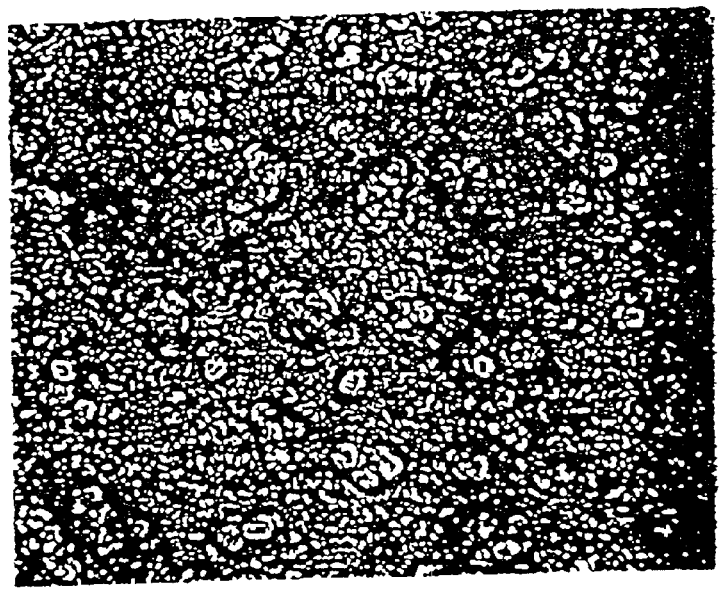

FIG. 20 is a photo magnification×200) of delta insulin produced by a rapid cooling down profile and vigourous stirring at 500 t/min (example 7).

Figure 21:
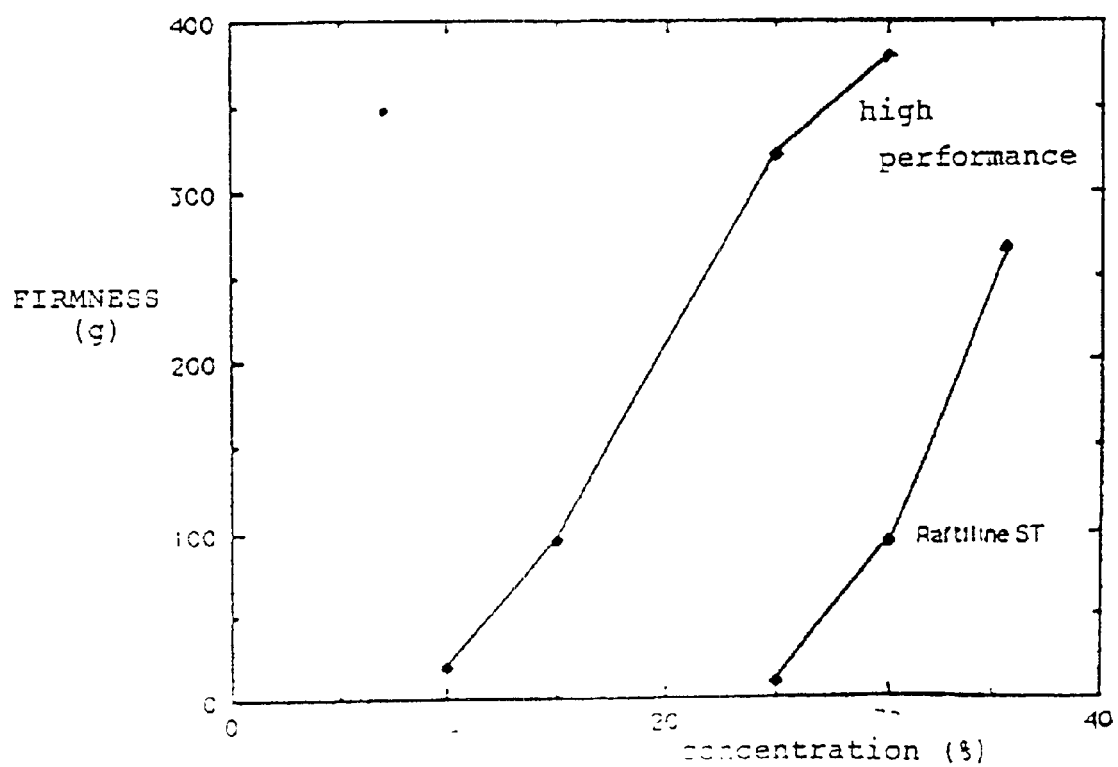

FIG. 21 illustrates the firmness of a cream of high performance Raftiline® as a function of the weight concentration in comparison to Raftiline® ST.

Figure 22:
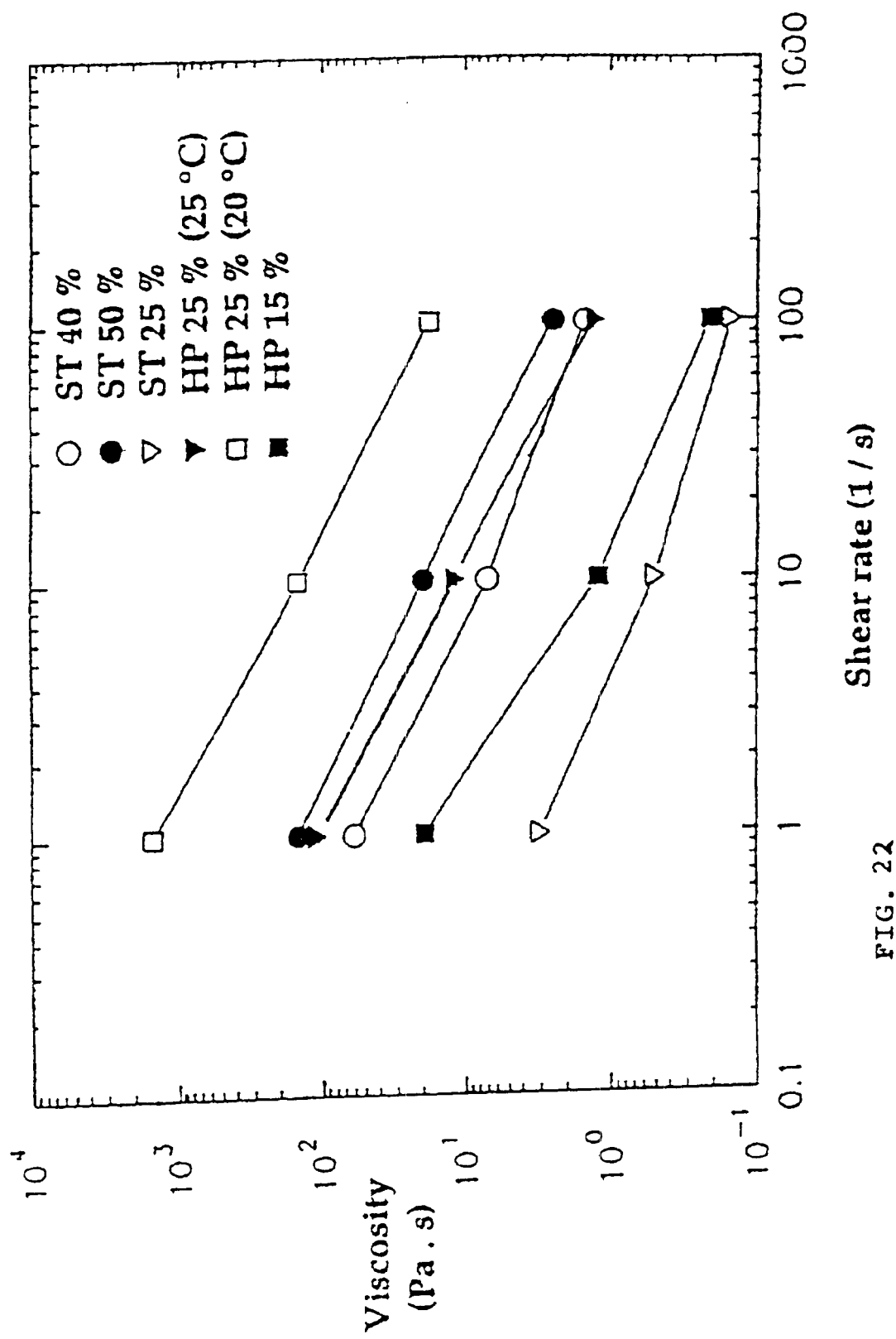

FIG. 22 illustrates the viscosity of a high performance Raftiline® cream.

Figure 23:
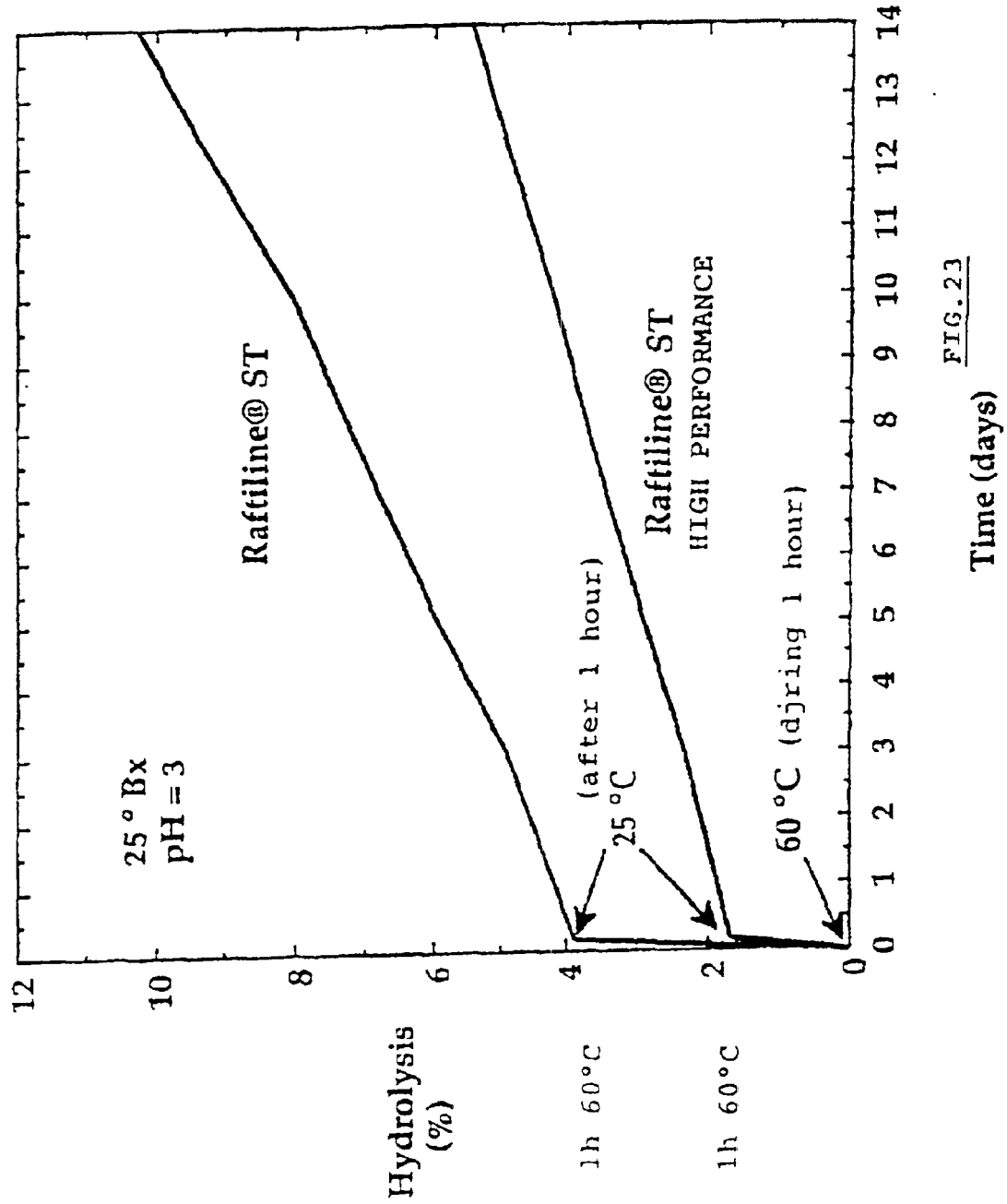

FIG. 23 illustrates the better acid resistance of high performance Raftiline® compared to Raftiline® ST.

DESCRIPTION OF A PREFERRED EMBODIMENT OF THE INVENTION

The invention relates to a new fractionated polydisperse inulin which combines four important characteristics in a single fractionated composition, i.e.:

an av. DP which is significantly higher than the av. DP of the native polydisperse inulin;

an inulin which is significantly free from low molecular monosaccharides, disaccharides and oligosaccharides; and an inulin which is significantly free from impurities chosen among the group consisting of colourings, salts, proteins and organic acids; and an inulin which is free of technological aids such as solubility affecting products.

A preferred fractionated polydisperse inulin is an high performance inulin (which is spray-dried) and which in addition to the four characteristics of the new fractionated polydisperse carbohydrate composition, has also one or more of the following properties compared to known inulin compositions:

is acariogenic,
shows a better tolerance pattern,
does not have a sweet taste,
is less soluble,
shows higher viscosity in solution and in suspension,
makes a more firm cream,
has a lower calorific value,
has better acid resistance,
has an anti-cacking effect,
shows a lesser hygroscopicity,
has no reducing capacity,
is less sticky in the solid fore or as a cream,
shows improved thermal stability,
causes no problems in processing due to colouring,
shows a higher resistance to breakdown by bacteria and yeasts,
is better suited to chemical modification,
has a higher melting point,
has neutral taste,
is odour-tree.

Figure 1:
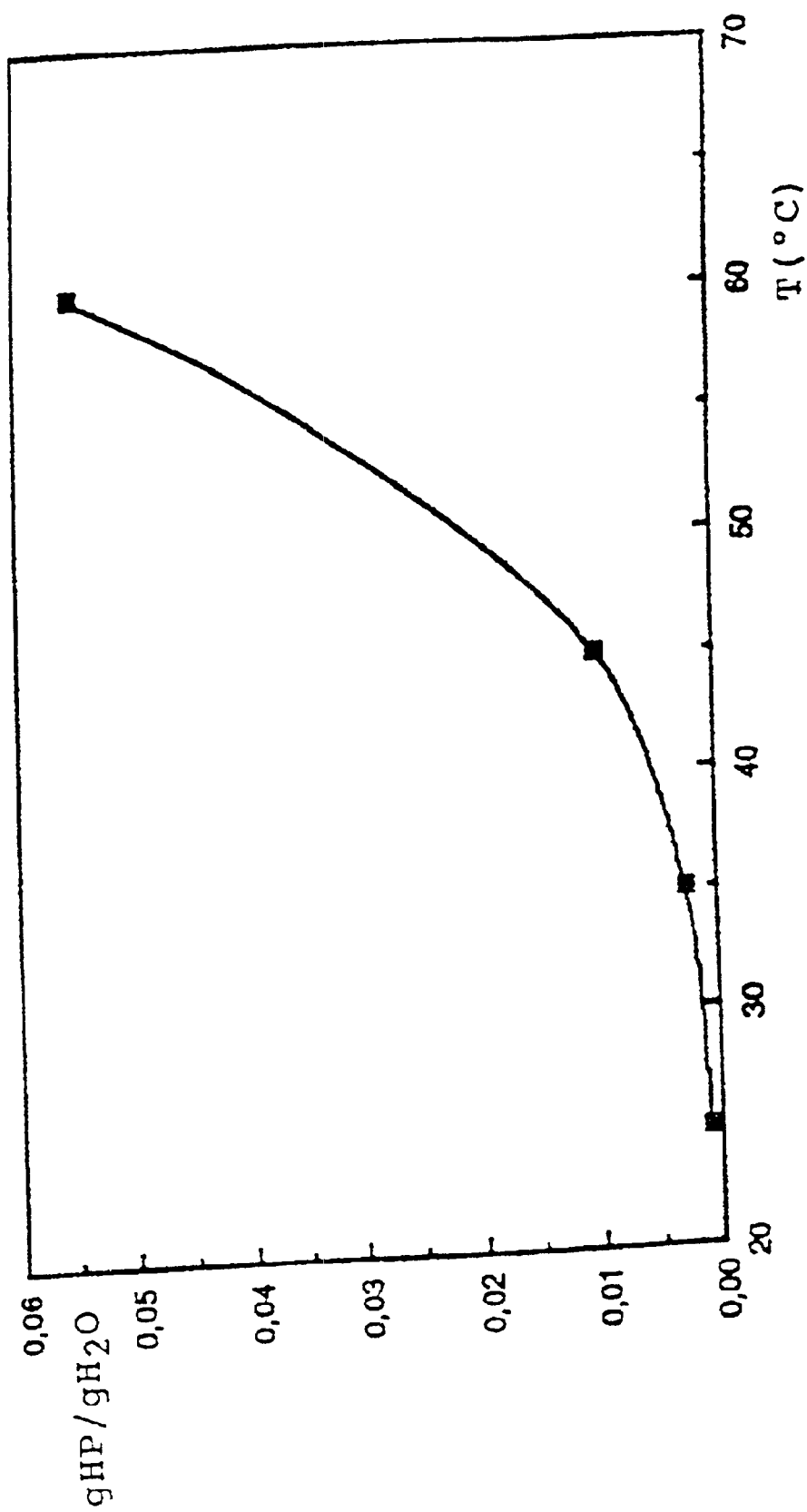
FIG. 1 shows a solubility curve for high performance Raftiline® in g/g H:O as a function of temperature.
Figure 2:
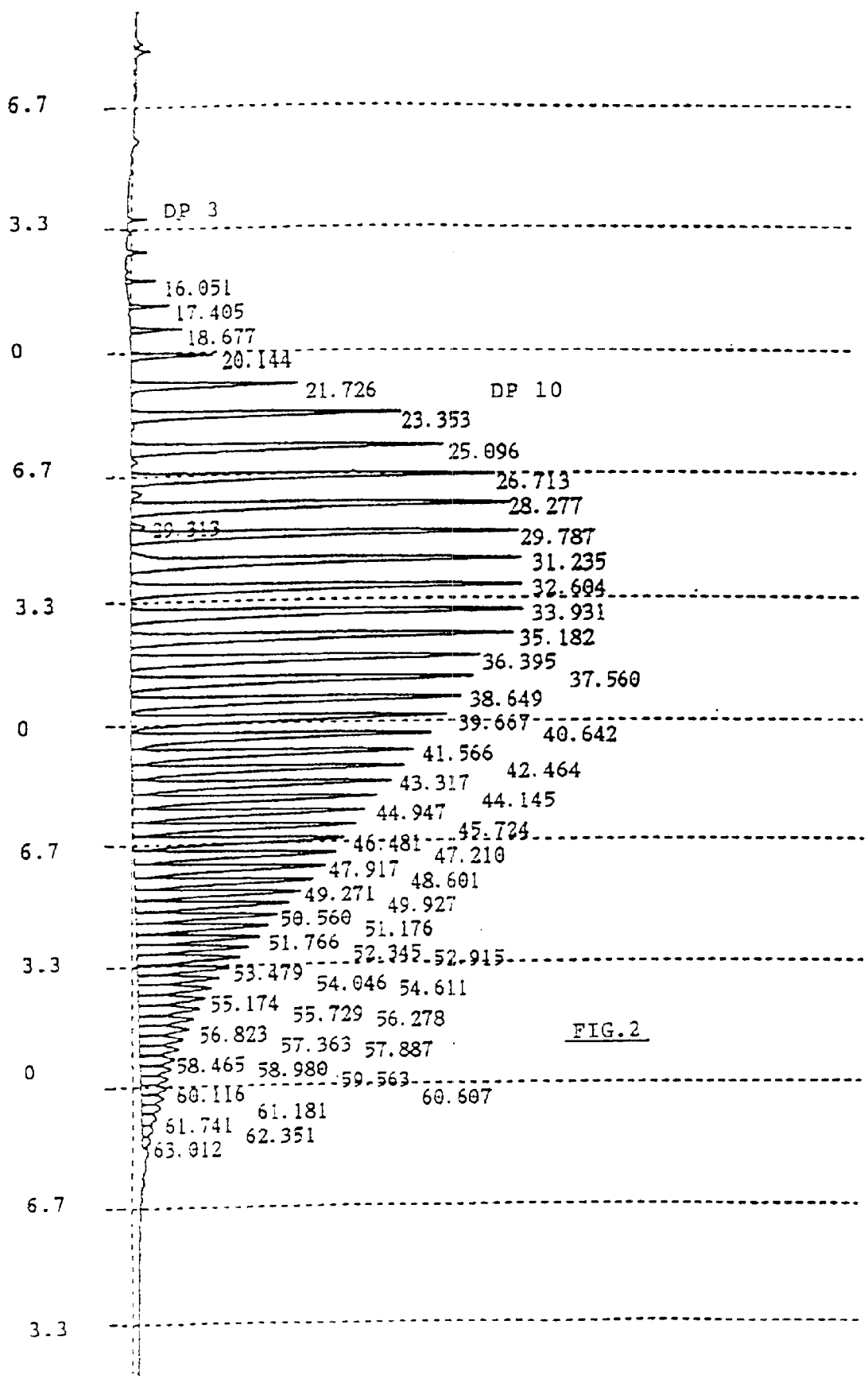
FIG. 2 shows a DIONEX analysis of high performance Raftiline®.

A preferred high performance inulin is high performance Raftiline® with chicory inulin molecules and:

an av. DP between 20 and 40, more particularly between 20 and 35, specifically between 20 and 30 and preferably between 23 and 27,
a maximum DP which is in the range 60–70,
a typical solubility as indicated in FIG. 1,
a typical DIONEX as indicated in FIG. 2,
a typical gas chromatography analysis as indicated in FIG. 3.

Figure 4:
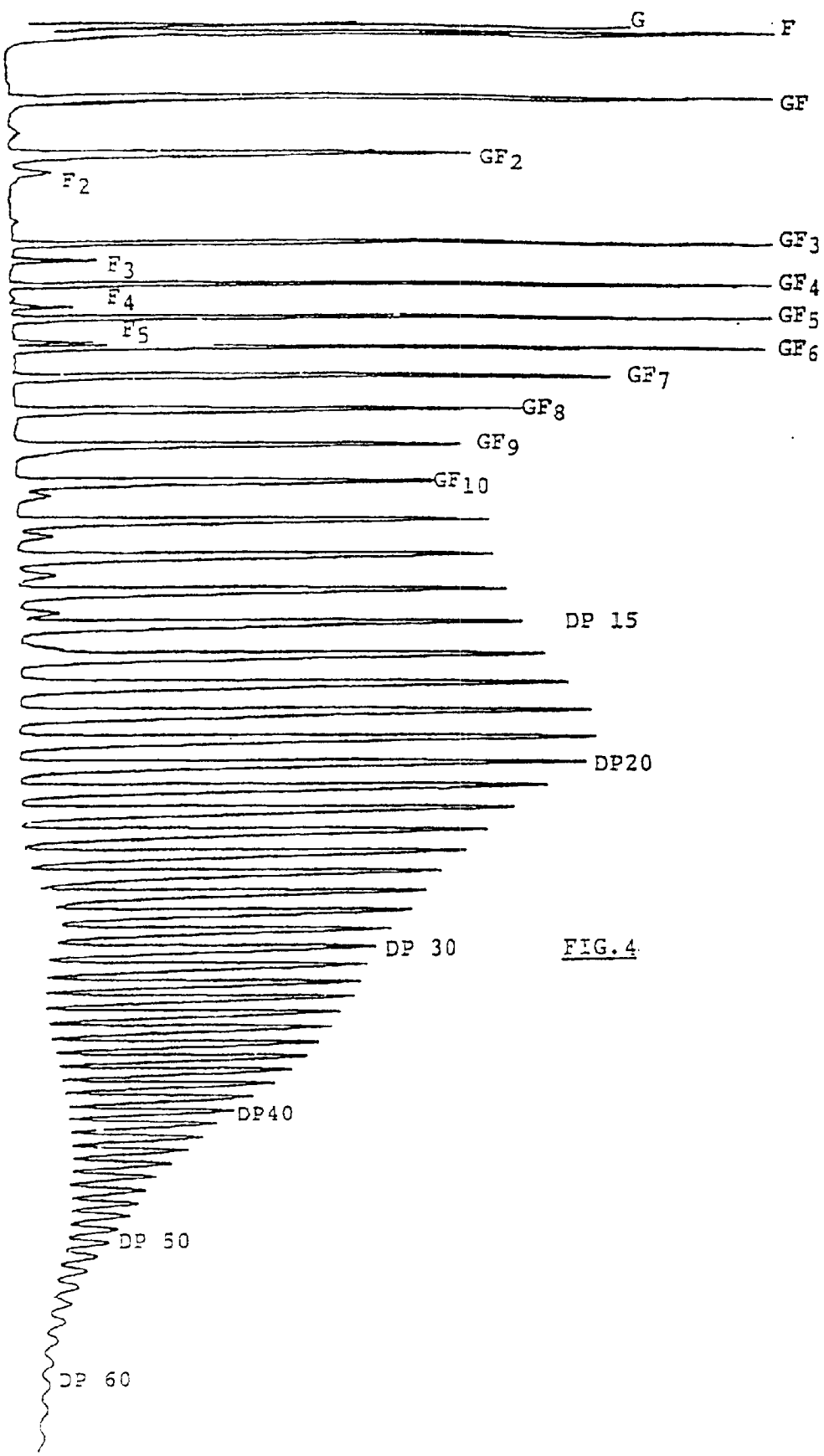
FIG. 4 shows a DIONEX analysis of Raftiline® ST.

A DIONEX for Raftiline® ST is given in FIG. 4 as a comparison.

The term "a significantly higher av. DP" compared to the native polydisperse carbohydrate composition means that said av. DP is almost double of even higher.

The term "significantly free of monomers or dimers" means a composition containing less than 0,2 wt % of monomers or dimers, more preferably less than 0,1 wt % of monomers or dimers.

Advantageously, said composition comprises less than 1,5 wt % of oligomers with a DP<10.

The term "significantly free of impurities" means that the ash amount in the composition according to the invention is less than 0,2 wt %, preferably less than 0,1 wt %.

The term "free of technological aids" means that no technological aid can be detected in the composition, more specifically no alcohol like methanol, ethanol, isopropanol, . . . .

The applicant has also identified and isolated a new crystallized form of fractionated polydisperse inulin: "delta inulin".

Delta inulin is a crystallized inulin with a high av. DP consisting mainly of spherical particles with a diameter of 1 to 100 μm, more specifically 5 to 70 μm. and even more specifically 6 to 60 μm (see FIGS. 5, 6 and 7). The delta inulin particles have a radial symmetry, are double breaking with a perpendicular fade cross (Maltezer cross) under polarised light (see FIG. 8).

Because of its purity in the solid state, delta inulin can be used for he industrial preparation of fractionated polydisperse inulin on a large scale and in a straightforward manner.

The spherical inulin particles contain no quantifiable enclosed impurities or low molecular saccharides.

The crystallised inulin molecules with a high DP as occurring in the delta inulin have such a spherical morphology that they make smooth industrial physical separations possible.

Due to their spherical structure they unexpectedly also allow the removal of impurities and low molecular carbohydrates by means or washing. Said property simplifies the preparation process of the composition according to the invention.

Other properties of delta inulin are:

a higher resistance to enzymatic degradation,
a higher resistance to acids,
no sweet taste,
a lower solubility.

The delta inulin can be obtained in a dry powder by drying the solid Form after nucleation using systems which permit the drying of compositions with a high dry material content. Preferably, a fluid bed dryer, a flash dryer, a tunnel dryer or a ring dryer is used.

Delta inulin, high performance inulin and high performance Raftiline® can be obtained by using the new crystallisation process according to the invention.

The applicant has recognised the unexpectable fact that for a solution of polydisperse carbohydrate molecules, the rapid achievement of a high degree of super saturation results in particles which consist entirely of molecules with a high DP and a spherical morphology. These particles allow a smooth and industrially applicable physical separation and greatly simplify he removal of impurities and molecules with a low DP through washing.

Said directed crystallisation of a solution, in accordance to the invention, is characterised by the rapid achievement of a high degree of super saturation, obtained either through a rapid cooling down involving an important temperature modification, a rapid concentration increase involving an important concentration modification, or by a combination of both.

The directed crystallisation according to the invention is obtained for chicory inulin but may also be applied to the preparation of high DP inulin fractions from other sources.

Other sources of production are e.g. inulin from natural sources which include plant types such as dahlias, Jerusalem artichokes, allium, bananas, onions, yacou, uriginea maritima, etc. It is also possible to apply the principle to polydisperse polymer compositions of the inulin type which are produced by biotechnological synthesis such as in vivo or in vitro enzyme synthesis.

When the solubility of the various polymer fractions is different, in general all polydisperse carbohydrate compositions or modified polydisperse carbohydrate compositions can be fractionated using said directed crystallisation process. It is possible for a man skilled in the art to adapt the parameters as here elaborated for chicory inulin when a different source of inulin or a different polydisperse carbohydrate composition is used.

Preferably, the polydisperse carbohydrate compositions which are fractionated with said process are fructans and they have preferably mainly β-linkages between the carbohydrate units.

In order to separate out a very specific fraction, it is possible to carry out several directed crystallisations in sequence on the same polydisperse compositions.

The invention therefore relates also to polydisperse carbohydrate compositions consisting of a mixture of various fractionated compositions according to the invention. It is within the competence of the man skilled in the art to obtain these mixtures, depending on the desired end result. In other words, the invention allows also to obtain pure fractionated polydisperse carbohydrate compositions which improves the development of "tailor made" mixtures to meet the requirements of the professional in each specific field of application.

As already stated, native chicory is used as the starting product for working out directed crystallisation. This may be applied to a raw extract, demineralised raw extract or fully refined inulin.

The directed crystallisation process according to the invention, allows the fractionning of whatever type of inulin of whatever degree of purity, and therefore makes possible the quantitative separation of inulin molecules with a high DP, substantially free of impurities and free from low molecular saccharides. In other words the directed crystallisation permits the preparation of the new fractionated polydisperse carbohydrate compositions according to the invention.

More specifically, a preparation of fractionated polydisperse carbohydrate compositions comprises the following steps:

preparation of a metastable solution of a native polydisperse carbohydrate composition, a directed crystallisation of said solution, separation of the formed particles, which may be followed by washing of the separated particles, and drying of the obtained particles.

A native polydisperse carbohydrate composition is defined as the original polydisperse carbohydrate composition which needs to be fractionated.

In order to prepare a solution in the case of native inulin it is clear to the man skilled in the art that the solubility is dependent on the temperature of the solution and the av. DP of the polydisperse inulin composition.

In order to carry out directed crystallisation it is necessary to bring the native inulin fully into solution. In the case of native chicory inulin, an inulin solution is used with a concentration of between 15 and 60% DM and where possible between 25 and 50%. There are many reasons for this. Inulin as a solid form has a tertiary structure (W. D. Eigner, Physico-chemical Characterization or Inulin and Sinistrin, Carbohydrate Research, 180, (1988), p 87), which must be broken down before inulin of the delta type can be formed. Moreover in the case of solid native inulin there may be impurities contained in the tertiary structure which prevent the production of pure end products.

The tertiary structure of inulin can be broken down by subjecting the inulin to high temperatures, but also to ultrasound, high friction powers and/or ultrasonification. Where chicory inulin is concerned, it is known that (from WO 94/12541 for instance) subjecting it to high temperatures can bring native inulin fully into solution. The higher the temperature used, the lower may be the contact time.

When an inulin solution is kept at a high temperature for too long the chances of chemical breakdown, colour forming, hydrolysis and the formation of molecules with a low DP become greater. These problems are a function of the pH. In order to avoid them it is recommended that the inulin should be processed as quickly as possible at a pH of between 5 and 7.

When this dissolved Inulin as now brought down to a lower temperature (60 to 70° C.) the inulin will first of all be in a metastable condition as described in WO94/12541. This means that despite the temperature of the solution being lower than the minimum solubility temperature there is for the time being no spontaneous nucleation. The time necessary before nucleation starts depends on the concentration of the metastable inulin solution. The less the temperature deviates from the minimum solubility temperature and the lower the concentration, the longer the time needed before nucleation takes place and thus inulin particles spontaneously precipitate.

By subjecting the inulin solution to a directed crystallisation process according to the invention, the particle formation will take place in a directed manner.

Figure 9:
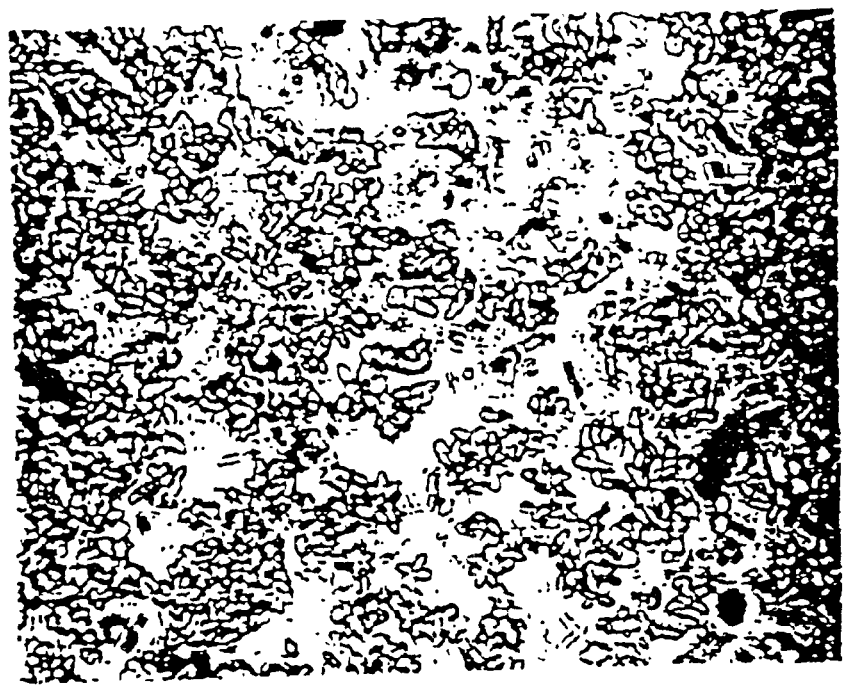
FIG. 9 is a photo (magnification×200) of an inulin suspension produced by spontaneous particle formation at a constant temperature of 60° C. (example 1). Ellipsoid particles can be seen.

Indeed, a metastable chicory inulin solution of e.g. 45% DM at a constant temperature of 60° C. will precipitate spontaneously after approximately 1 hour. The particles formed in such circumstances are "ellipsoid" and show the two-part structure as illustrated in FIG. 9. The rate of growth and/or the increase in the number of ellipsoid particles during spontaneous precipitation remains dependent on the concentration of the metastable inulin solution. As shown in the examples below, such particles in practice turn out to be difficult to handle and the separation of these on an industrial scale is not viable.

Directed crystallisation of metastable chicory inulin results in a suspension of spherical particles with a diameter of between 1 to 100 µm. more specifically 5 to 70 µm and even more specifically 6 to 60 µm, which is called delta inulin. For an illustration see FIGS. 5 to 7. This is in contrast to the usual known crystallisation phenomena. The normal rule is that a higher degree of super saturation, achieved through rapid cooling down or rapid increase of concentration causes an increase in the number of stable nucleates. Normally the result of this is the formation of very large numbers of very small particles. This hinders the smooth separation of such particles.

The applicant has recognised the effect of the rapid achievement as a condition of super saturation and applied the same for the development of a new preparation process which allows polydisperse carbohydrate compositions to be fractionated on an industrial scale with a high degree of purity. The particles which are created by a directed crystallisation have a shape, diameter size and negligible standard deviation of the average diameter.

Thus, it is possible to separate these particles smoothly from the parent lye and con the other hand to carry out thorough purification by simple washing. The regular stacking of spheres prevents clogging, and thus impurities located in the interstitial spaces between the particles can be washed away.

Moreover the particles are formed in such a way that impurities and/or low molecular weight saccharides are not enclosed within the solid form.

Figure 5:
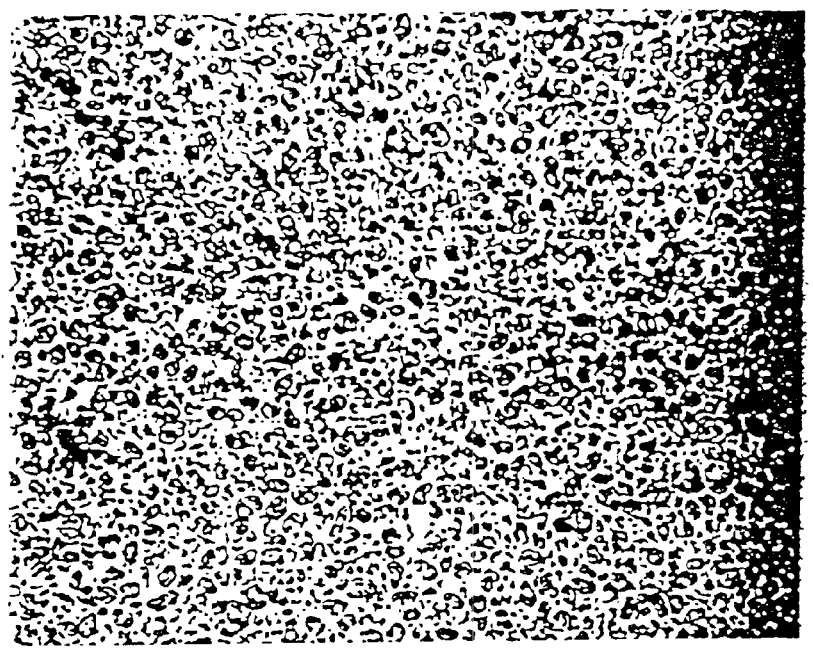
FIG. 5 is a photo (magnification×200) of delta inulin with an average particle diameter of 7.7 µm (standard deviation ±0.7 µm)
Figure 6:
FIG. 6 is a photo (magnification×200) of delta inulin with an average particle diameter of 20 µm (standard deviation ±2.5 µm)
Figure 7:
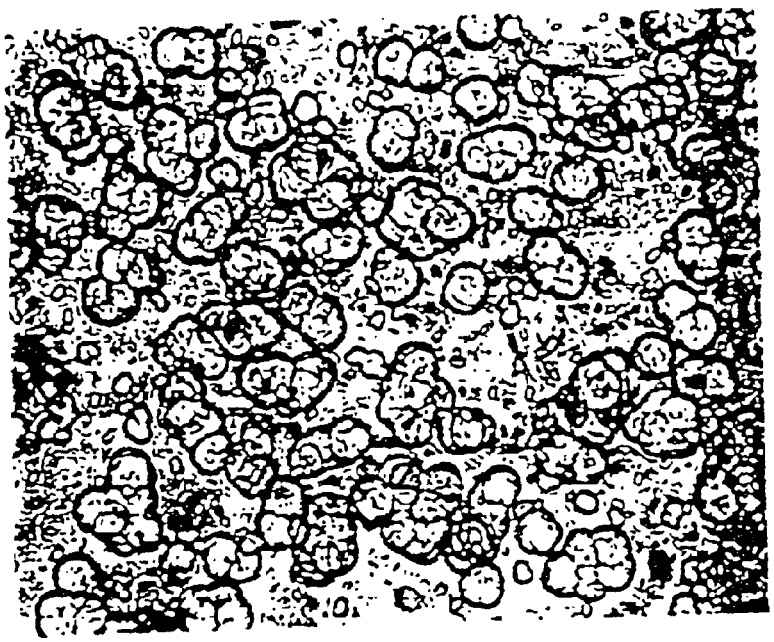
FIG. 7 is a photo (magnification×200) of delta inulin with an average particle diameter of 44 µm (standard deviation ±5 µm)
Figure 8:
FIG. 8 is a photo (magnification×500) of delta inulin with a particle diameter of 20 µm under polarised light. The fade crosses can be clearly seen.

The standard deviation of the average diameter of the particles produced when a specific polydisperse carbohydrate composition is fractionated according to the invention has a maximum of 25%, preferably 15% and more specifically 10% (see thee legend of FIGS. 5 to 7). The particles allow a stacking of spheres thus obtained without compacting.

Figure 10:
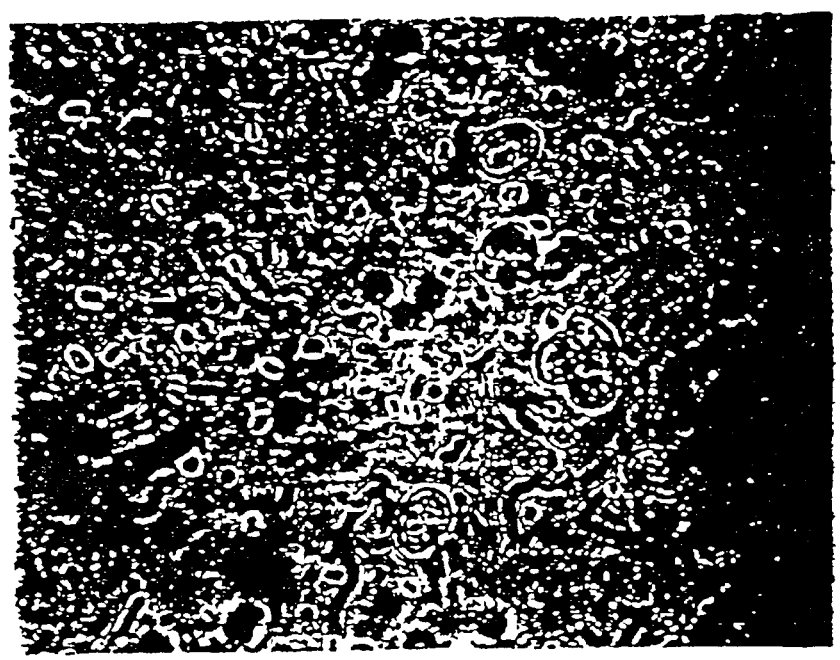
FIG. 10 is a photo (magnification×200) of an inulin suspension produced by spontaneous particle formation during a slow cooling down pattern (example 2). In addition to the large particles, small particles can also be seen.

For comparison, it should be observed that a metastable solution which is slowly cooled down to a low temperature contains both spherical and ellipsoid particles as well as others with different shapes (see FIG. 10). Particle stacks such as these will certainly "clog up".

Directed crystallisation through cooling down can be characterised as follows. The more rapidly the cooling down takes place, the more uniform the particles. The lower the cooling down temperature, the larger the particles and the quicker a given yield for particle formation is achieved. The rate of growth of particles at a lower cooling down temperature is higher than the rate of nucleation. Conversely, at a higher temperature the rate of nucleation will be higher than that of the rate of particle growth.

Cooling down of the metastable solution is preferably to be achieved by means of heat exchangers. Rapid achievement of super saturation through increases in concentration is preferably to be achieved through evaporation.

In the specific case of the fractioning of native inulin from chicory roots obtained with the directed crystallisation process, the rate of cooling down is between 0.2 and 10° C./sec, more particularly between 1 and 7° C. sec and by preference between 2 and 5° C./sec.

Native inulin from chicory roots is brought into solution by allowing the inulin to maintain a temperature of above 85° C. for the necessary period of time. Then the metastable solution is prepared and very rapidly cooled down to a temperature higher than the coagulation temperature of the solution, preferably a temperature between −6° C. and 40° C., more specifically between 15 and 25° C., and preferably between 20° C.±3° C.

If required, the diameter and the distribution profile of the particles according to the invention can be influenced by e.g. the use of grafting particles. The grafting suspensions may originate from particles previously formed through directed crystallisation as such or from these particles after they have undergone further purification.

The grafting solution can be prepared by the dilution of the suspension described above with water. As a general rule the higher the added dose of grafting particles, the greater the number and the smaller the size of the particles which are then formed through directed crystallisation. This is analogous to the classical influence of grafting.

The use of grafting crystals may optimize directed crystallisation, but must not be carried out in such a way that the same condition is created as in precipitation at higher temperatures or when using a slow cooling down pattern. In particular, the formation of particles smaller than 1 μm causes problems, since a suspension containing such particles is difficult to separate due to the formation of compact stacking and moreover permits washing only with difficulty.

When the directed crystallisation process according to the invention is carried out in accordance with the invention using native inulin from chicory roots and grafting is employed; a specific diameter between 1 and 100 μm can be obtained with the quantity of grafting particles in ratio to the particles to be produced at 1/100 to respectively 1/200,000 (expressed as wt %).

If a particles diameter between 5 and 50 μm is wished, a ratio of 1/5000 to 1/80,000 (wt %) respectively is used.

The diameter and distribution profile of the particles can also be influenced by stirring during particle formation. In an equivalent manner, too high a stirring speed will no longer serve to optimize the preparation process but tend towards a condition of uncontrolled precipitation which is to be avoided. The particles formed by crystallisation are fragile. Where they are subjected to pressure or exposed to mechanical forces the particles degrade and become small shapeless fragments. Too vigorous stirring of the particle suspension created by directed crystallisation can have the same effect.

Once directed crystallisation has started, depending on the starting concentration of the polydisperse solution and depending on time, a certain yield of particles will be achieved. This yield is defined as the quantity of particles formed through directed crystallisation in ratio to the dry material present in the polydisperse solution and expressed as a wt %.

In the case of delta inulin a yield of 20 to 60% can be achieved.

The suspension of formed particles can now be filtered, centrifugated or subjected to whatever type of solid/liquid separation technique as used by the man skilled in the art to separate particles from the parent lye.

These solid/liquid separation techniques are however unable to remove the whole of the liquid phase from the solid phase since the particles are still covered by a layer of water which contains the same concentration of impurities as separated out in the liquid phase.

Since these impurities are dissolved in the remains of the liquid phase and will accordingly make up part of the dried or non-dried end product, the separated particles still need to be purified by means of contact with a pure liquid, preferably water.

As already mentioned, particles formed by directed crystallisation are of such a nature that a pure end product can be obtained through simple washing. With the particles obtained, a simple displacement front of pure water can be put into place against the liquid phase and its impurities.

This is much less tedious than the usual methods. Indeed, for the purification of impure crystal suspensions recourse is normally made to multiple re-suspensions of the particles in pure water. For purification of impure crystals the solid material is dissolved several times, and each time recrystallised.

Washing efficiency is defined as the quantity of purified particles (expressed in kg) per kg of water used for washing. As with the degree of filtration, this is dependent on the form, diameter and distribution pattern in the solid phase. In a similar way, non-spherical structure, smaller particles and a broad pattern of diameter distribution would hinder access to the wash water. Particles formed in accordance with the invention are however spherical in shape, have a controllable size and are almost uniform, making simple washing possible.

It follows from this that crystallisation is not only essential for particle formation and separation but also for purification of the particle suspension by washing.

In the specific case of delta inulin the best results are achieved using demineralised water at 15° C. and vacuum filtration. The wash efficiency is optimal when use is made of a counter-current principle. The choice of temperature for the wash water may be made in accordance with the following: with the use of cold water the amount of solid inulin in particle form which will go into solution is brought back to a minimum and there is therefore almost no yield fall which can be identified. By the use of warm water (60° C.) the wash efficiency is higher but a significant amount of the solid inulin will go into solution, reducing the overall yield. An advantage of the use of warmer water is that the viscosity of the wash water falls, allowing a corresponding improvement in filterability.

Other solid/liquid separation techniques, apart from vacuum filtration, may be used. In the present case, special care needs to be taken of the effect of the higher pressure when e.g. work is done using a pressure filter system, with indirect higher pressure where a centrifugal force is employed and with the difference in density between the solid and the liquid phases when hydrocyclonic techniques are used.

For separation techniques for which high pressure differences are deployed, it must be taken into account that the particles are fragile and that they will degrade under high pressure and form particles that are too small and too irregular and/or form a colloidal suspension in the liquid phase. This is not a crucial problem for a crude separation but it will affect the washing.

For separation techniques based on differences in density, the extremely small density difference between the liquid phase and the solid phase must be taken into account.

The DM content of the cake obtained in the case of vacuum filtration of a delta inulin suspension varies between 30 and 70%. Delta inulin can then be dried using various drying techniques such as fluid bed dryers, ring dryers, tunnel dryers, etc. If drying takes place in a stiffening dryer, the filter cake should once again be thinned out to a suspension or a solution of up to 50% DM, preferably between 20 and 40% DM, and more specifically 30% using demineralised water.

High performance inulin can be prepared when the native inulin is subjected to the preparation process according to the invention and when directed crystallisation is characterized by rapid cooling down using an important temperature modification. The delta inulin produced following this directed crystallisation is once again thinned down, pasteurised and spray dried to from the final high performance inulin.

High performance inulin has improved and totally new properties. High performance Raftiline® can be obtained when native inulin from chicory roots is subjected to the preparation process according to the invention and the directed crystallisation is characterised by rapid cooling down using an important temperature modification. The delta inulin produced following this directed crystallisation is once again thinned down, pasteurised and spray dried to form the final high performance Raftiline®.

The invention also relates to fractionated polydisperse carbohydrate compositions which are sequentially subjected to the directed crystallisation process. In the case of fractionated inulin from chicory roots the av. DP may e.g. be increased by 5 DP units or more by bringing the fractionated inulin into the metastable solution once again and carrying out a second directed crystallisation process.

The solubility of the compositions according to the invention can be affected by the addition of other products such as salts, carbohydrates including saccharose and other sugars, sugar alcohols, starches or maltodextrines, gums such as xanthane, carob gum, guava gum, carboxymethyl cellulose, carrageenan, alginate, nutritional fibre, fats, or mixtures of these, generally called solubility affecting products.

The compositions according to the invention are free from impurities. Pure compositions according to the invention allow the amounts needed to affect solubility to be added in a controlled manner. Where the compositions according to the invention need to be dried the addition of solubility affecting products may have the additional advantage that lump formation is prevented. As a result the dried products quickly redissolve, or a stable and uniform cream may be produced.

More specifically, solubility affecting products may be added to both delta inulin and high performance inulin in the powder, solution or cream forms. These solubility affecting products may be added to the invention's compositions in the form of a concentrated solution or a watery paste.

The solubility of the dried compositions may also be improved by use of the process described in the Belgian patent application BE 93/00210, incorporated hereafter by reference.

Since the solubility of high performance Raftiline® is extremely low, this may rise to problems in applications where high performance Raftiline® needs to be used at higher concentration in a liquid. Since high performance Raftiline® is thermally stable however, it can be dissolved at high temperatures. When a heating process is used in the preparation process of a liquid product, high performance Ratline® can be added in a concentration of 0.1 to 5%, more particularly 0.5 to 4 and more specifically 1 to 3%.

The invention also relates to compositions whose solubility is improved by one of these foresaid methods.

The new compositions according to the invention are particularly suited for chemical modification. In order for chemical modification of a polydisperse carbohydrate composition to be successful, the polydispersity of the composition should be maintained. In other words there should be very little chain degradation, the molecule linkages should be maintained as much as possible.

Two types of chemical modifications are particularly preferred, one where the backbone of the polymer molecules are kept intact and a second where the backbone molecules are modified.

The particularly preferred fractionated polydisperse carbohydrate composition being fractionated fructans mainly build up of fructose, linked by fructosyl-fructose linkages, are successfully modified when the linkages are maintained and the chemical modification takes place on one or more of the three free OH groups of the fructose, respectively linked to the C2, C3 or C6 atom of the backbone fructose molecule or when the atom linkages of the fructose molecules are broken.

The chemical modifications on the free OH group can be subdivided into etherification reactions or esterification reactions. The degree of modification or substitution (DS) can be expressed in a number from 0 to 3 as an indication for the amount of modified or substituted OH groups present. A fully substituted fractionated fructan composition according to the invention will have a DS of 3. Is it substituted for 20% only, the DS will be 0,6.

Therefor, etherified or esterifed fractionated polydisperse carbohydrate compositions are an other objective of the invention. More particularly etherified or esterified fractionated fructans and etherified or esterified fractionated inulin are preferred.

Etherified fractionated inulin according to the invention with the following general formula I is particularly preferred:

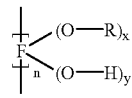

formula I
where:
  F is a fructose molecule,
  R is a branched or non branched saturated or unsaturated carbon chain of 1to 20 carbon atoms, eventually carrying functional groups such as COOH, CONH$_2$, NH$_2$, C≡N, OH, C=CH$_2$ or epoxide ring,
average n is between 20 and 40,
  x is between 0 and 3 and
  y is between 0 and 3.

The functional groups of an etherified fractionated inulin according to the invention can again react with a fractionated inulin and/or a chemically modified fractionated inulin, in order to obtain a cross linked end product. Such cross linked etherified fractionated inulins are particularly preferred chemically modified compositions according to the invention.

Esterified fractionated inulin according to the invention with the following formula II is equally particularly preferred:

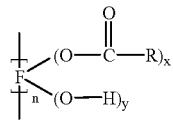

formula II
where:
F is a fructose molecule,
R is a branched or non branched saturated or unsaturated carbon chain of 1 to 20 carbon atoms, eventually carrying functional groups such as COOH, CONH$_2$, NH$_2$, C≡N, OH, C=CH$_2$ or epoxide ring,
average n is between 20 and 40,
x is between 0 and 3 and
y is between 0 and 3.

The functional groups of an esterified fractionated inulin according to the invention can again react with a fractionated inulin and/or a chemically modified fractionated inulin, in order to obtain a cross linked end product.

Such cross linked esterified fractionated inulins are particularly preferred chemically modified compositions according to the invention.

In order to prepare an etherified or esterified fractionated composition according to the invention, it is necessary that the nucleophilic character of the OH-groups be improved. This can be done either by deprotonising the OH groups or through the induction of a higher electron density around the O— atom. Such activation of OH groups can be obtained using reaction products with basic properties. These reaction products, generally called bases, can be basic catalysts such as ion exchangers, basic solvents such as pyridin, water soluble hydroxides such as sodium- or potassium hydroxides, salts of weak acids or combinations thereof.

When esterified or etherified fractionated chicory inulin is prepared, one can use more basic reaction conditions compared to the chemical modification of native chicory inulin. Typical side reactions such as brown colouring, formation of breakdown products and depolymerisation reactions are avoided. Yield is improved.

The chemical modification whereby the atom linkages of the molecules of the polymer backbone are broken is another type of chemical modification typically suited for fractionated polydisperse carbohydrate compositions according to the invention.

As such when fractionated fructans are modified by oxidising the fructose ring, for example, the C2–C3 linkage is broken and the C2 and C3 atoms are oxidised to aldehyde and/or carboxyl functions.

The oxidation can be obtained using hydrogen peroxide, oxygen, periodic acid, hypochloride, hypobromide and sodium bromide or with other oxidising substances eventually in the presence of a catalyst.

Oxidised fractionated inulin is a particularly preferred embodiment of the invention. Fractionated chicory inulin is very stable, taking into account the aggressive oxidative reaction conditions. As such dicarboxy chicory inulin obtained using the fractionated chicory inulin according to the invention is still a polydisperse composition with an av. DP higher than the av. DP of the native chicory inulin.

A specifically modified fractionated fructan according to the invention is the product whereby the oxidation is limited to the C6 atom, by modifying the primary alcohol function to the corresponding aldehyde- and further on to the corresponding carboxyl function. Here no atom linkage of the ring is broken and therefore no ring opening occurs. Carboxymethyl inulin is a typically preferred example of such a specific embodiment of the invention.

The new fractionated polydisperse carbohydrate compositions also lend themselves to enzyme modification according to well-known methods using e.g. hydrolases, transferases, esterases, . . . .

The invention accordingly relates to products produced by enzyme modification of the new fractionated polydisperse carbohydrate compositions, more particularly to the new fractionated fructan compositions and more specifically the new fractionated inulin compositions.

This invention also relates to a composition in the form of a cream. The cream may be prepared by applying the Rafticreaming® system as described in WO 93/06744 to the composition in accordance with the invention. The invention relates more particularly to a cream which contains the fractionated fructans, even more particularly to fractionated inulin and more specifically to fractionated chicory inulin (also called high performance Raftiline® cream)

A composition in the form of a cream offers a number of advantages in comparison to the same composition in the form of a powder, suspension or solution when it is added as an ingredient to food products or as a component in other products.

The use of a cream containing no high performance inulin results for instance in a fattier taste, a more creamy feeling in the mouth, a smooth texture, a brilliant appearance, a more viscous feeling, more taste, no after taste, no dry feeling in the mouth or on the skin etc. The minimum concentration at which a cream can be produced is approximately 10 wt %.

For Rafticreaming®, in principle any type of mixing device which generates shearing forces and which disperses the HP inulin powder without fully dissolving it may be utilised.

The viscosity, firmness and thermal stability of the cream increases with the rise in the high performance inulin concentration. These qualities may however also be affected by the method of preparing the cream by changing for instance the mixing device, the temperature or pressure, as well as by the presence of other ingredients such as sugars, hydrocolloids, proteins, fats, salts, . . . .

As already mentioned, taking into account the fact that the solubility of the compositions according to the invention can be affected in a number of ways, this factor can be used to affect the formation of the cream. In this way a whole range of HP inulin creams have been produced, using concentrations varying between 2 and 60%. Preference is given to creams of between 5 and 50% and more specifically 10 to 20%, whether or not produced with the addition of a solubility affecting product.

One specific area of application for the compositions according to the invention is as a substitute for fats and/or oil in food products. Replacement of triglycerides can be effected in a proportional manner when it is based on the total weight of the fats or oil replaced by the compositions according to the invention in the form of a cream.

Replacement or triglycerides can also take place using a combination of the compositions according to the invention together with other fat or oil replacements such as levans, dextran, starch., maltodextrine, proteins, microcrystalline cellulose, pectin, gum (guar gum, locust-bean gum, xanthane gum, . . . ), gels, . . . and/or mixtures of the same.

Other combinations with products such as thickeners, gelling products, emulsifiers etc. can also be used to partly or wholly replace triglycerides.

High performance inulin can for instance be combined with gelatine for the preparation of water-in-oil or water-continuous spreads.

High performance inulin can not only be used in products with lowered triglyceride levels, but also in ordinary products with the usual fat levels. High performance inulin can be used in these products to improve viscosity, firmness, creaminess, sheen, the feeling in the mouth etc. or to replace other ingredients (milk powder, starch, butter, gelatine, cheese etc.) and by so doing probably reduce the price of the goods.

The viscosity of hard boiled confectionery products can likewise be improved by the use of high performance inulin.

The applicant has for instance established that the invention's compositions in the form of a cream can be used in a simple and efficient manner as a stabiliser and anti synergetic agent in various food products, emulsions and mousses. High performance inulin for instance stablises the whipped-up structure of fillings, low fat cream or chocolate mousse. In such cases a cream is often better than inulin powder.

In a yoghurt for instance to which 10% Raftiline® cream and 25% DM is added, the milk whey will be preserved even after a long period of storage.

The creams according to the present invention are also especially suited for adding water to lipophile products as earlier described in WO93/06737 (Tiense Suikerraffinaderij, Belgium). Eminent examples of these are chocolate and chocolate paste.

Other typical applications where a composition in both powder and cream form can be used are based on the replacement of sugar as bulking agent or for the preparation of sugar free acariogenic or unsweetened products.

Sugar-free products preferred in the food sector are chocolate, candy, chewing gum, fillings, desserts, etc. Food products for which a sweet taste needs to be avoided but where sugar fulfils a technological function are e.g. meat products, spread pastes, cheese, sauces, sours and savoury snacks.

Other possible food applications are fruit preparations, milk products, ice cream yoghurt, soft curd cheese, pastry and patisserie, sorbets, cakes, and beverages ranging from lemonade to milk.

Since high performance inulin is more resistant to microbial breakdown, its use is to be preferred in food applications where fermentation takes place such as bread making for example.

The acid resistant characteristics of high performance inulin allow the addition of high performance inulin to more acidic environments such as e.g. salad dressings, Jams and soft drinks in the food sector. Only 0.7% of high performance Raftiline® is hydrolysed for instance at a pH of 3.5 at 95° C. over a period of 5 minutes.

In addition to the application of high performance inulin for food products, its application is likewise possible in cosmetic products (such as in emulsions of the o/w and the w/o type). HP inulin can be applied here as a provider of consistency which hinders the drying out of the product and promotes its easy and uniform application qualities, giving a pleasantly soft feeling to the product. The price can be lowered, the sheen of the product is improved and its hydrating effect remains noticeable over a longer period of time without any feeling of stickiness.

The applicant has also discovered that the composition according to the present invention may also be used as bridging systems/components, gels, protective coatings, carriers, as metal ion bindings, as polymer systems modifiers, for slipping, sliding and for the flow control, and/or for the modification and the stabilisation of interfaces.

The methods of analysis used are described in L. De Leenheer, Starch/Stärke 46, (1994), p 193.

The invention will be described in the following examples in more detail without thereby restricting the uses for the invention as already indicated above.

EXAMPLE 1

Spontaneous Particle Formation at a Constant Temperature of 60° C.

A metastable chicory inulin solution of 45% DM at 60° C. begins to precipitate spontaneously after one hour. The ellipsoid particles which are formed in this way can be seen in FIG. 9.

The filterability of these ellipsoid particles is 0.2 g suspension/min.cm$^2$ (Buchner filter, Whatmen no.1 filter paper). This filterability is extremely low and would require a very large surface area for filtration on an industrial scale.

EXAMPLE 2

Spontaneous Particle Formation with a Slow Cooling Down Pattern

A metastable chicory inulin solution of 45% DM which undergoes a slow cooling down pattern from 80° C. to 25° C. during a period of five hours will start to precipitate spontaneously after about 90 minutes. The particles which result show little uniformity and there is a large spread in the size of the particles. A portion of the particles are spherical, a portion have taken on a random form and a portion of them are ellipsoid, as can be seen in FIG. 10. On filtration the filter is clogged very quickly.

EXAMPLE 3

Preparation of Delta Inulin

A solution of 45DM is made using Raftiline® ST (Tiense Suikerraffinaderij, Belgium) and water at 65° C. The whole is well stirred in order to achieve a suspension that is as uniform as possible. Following this the suspension is pumped through a steriliser, after which the suspension will go into solution. Both the time period and the temperature profile which the inulin undergoes are shown in FIG. 12. This treatment has a threefold aim. On the one hand there is the bringing of the inulin into solution, on the other sterilisation and finally bringing the inulin into a metastable condition. The solution's pH is 6.

After leaving the steriliser, a grafting solution is added to the metastable solution with the aid of a peristaltic pump in the ratio of 1/20,000 wt % (grafting particles/inulin particles). This grafted metastable solution is then rapidly cooled by means of a heat exchanger to 20° C. and fed into a tank.

The precipitation begins after about ten minutes. The particles formed show a spherical structure with a diameter of the order of 25 μm. The filterability is 4 g suspension/ min.cm² and is thus better by a factor of 20 than the filterability of a spontaneous precipitation during a slow cooling down pattern.

After approximately two hours at 20° C. the yield from particle formation amounts to 35% and the suspension is filtered. The suspension thus obtained is sensitive to mechanical damage and behaves thixotropically. The filtration takes place using a band filter, a counter current principle and a controlled vacuum. In addition to water, the filter cake still contains a number of impurities in the interstitial spaces of the suspension. The filter cake is washed with demineralised water at 15° C. The filter cake washed in this way has DM of 41.9% and is free of impurities. (see FIG. 13).

The particles produced are characterised as delta inulin with the following characteristics: inulin with a DP of 25.8 in a solid form in the shape of spherical particles with a diameter of 25 μm (See FIG. 15) and with a standard deviation of 15%, by which the particles permit the formation of a spherical stack which does not compact. The delta inulin particles have a radial symmetry, are double breaking, with a perpendicular fade cross under polarised light.

EXAMPLE 4

Evolution of the Composition During Fractionation

Delta inulin is prepared according to the process described in example 3 starting with a raw carbonated inulin extract from chicory roots. FIG. 16 shows the reduction in ash content and monosaccharides, disaccharides and trisaccharides in the filter cake after washing.

EXAMPLE 5

Preparation of High Performance Inulin

Delta inulin prepared according to example 3 is brought into suspension once again with demineralised water to a 25% DM level and sterilised. The solution is spray dried using a spray dryer with an intake temperature of 185° C. and an outlet temperature of 85° C. The powder obtained has a DM content of 98%.

EXAMPLE 6

The Effect of Grafting

Two metastable solutions are prepared in accordance with example 3. One is grafted with particles formed during a previous directed crystallisation. The grafting solution is a 0.1% DM solution which has been diluted 20 times. Both solutions are subjected to the same directed crystallisation and after 24 hours the recording is made as shown in FIG. 16 and FIG. 17.

EXAMPLE 7

The Effect of Stirring

Three metastable solutions prepared in accordance with example 3 are either not stirred, stirred at a low speed of 20 rpm or vigorously stirred at 500 rpm The results are given in FIG. 18, FIG. 19 and FIG. 20 respectively.

EXAMPLE 8

Preparation of a Cream using High Performance Raftiline®

Pour 300 ml of water at room temperature into a beaker and place a Silverson L4RT in the beaker. Allow the Silverson to rotate at a maximum speed of ±8000 rpm and add 100 g of high performance Raftiline® little by little so as to prevent lumps from forming. Allow the Silverson to rotate for approximately a further 5 minutes after the Raftiline® has been added.

The high performance Raftiline® cream will begin to form shortly after the full suspension of the high performance Raftiline® powder. Depending on the concentration, cream formation will be clearly seen very quickly or only after several hours. The cream formed is white and opaque. It shows a short texture, similar to that of fats. It is thixotropic, stable, and shows no sagging or flocculation. The minimum concentration at which cream is formed is approximately 10 weight %.

Other mixing devices apart from the Silverson have been used for the preparation of the cream. In principle all appliances which generate shearing forces and which disperse the Raftiline® powder without completely dissolving it are eligible.

The hardness (FIG. 21), viscosity (FIG. 22) and thermal stability of the cream will rise with an increasing concentration of high performance Raftiline®. A high performance Raftiline® cream of respectively 20, 30 and 40 weight % is thermally stable to a temperature of respectively 80, 90 and 100° C. These properties may, however, be affected by the manner in which the cream is prepared and also by the addition of other ingredients.

EXAMPLE 9

Preparation of a Cream

Into a beaker of 1 l is poured 300 ml of water at room temperature and an Ultra-Turax T25 (Jenke & Kunkel) is placed in the beaker. While the Ultura-Turax is mixing at full speed 100 g of high performance Raftiline® is added in small quantities in order to prevent lumps from forming. After all the Raftiline® has been added the mixing continues for another ten minutes. During this time the cream already begins to form. The Raftiline® cream is white and opaque, has a fatty texture with pseudo plastic qualities, has a thixotropic rheological behaviour, is stable and no decantation or flocculation takes place.

When 850 ml of water and 150 g of Raftiline® is used, the cream forms at room temperature only after 2 or 3 hours and the cream is less firm. The cream will form more quickly in the refrigerator.

If boiling water is used for the cream then only a >24% DM mixture will allow the formation of a Raftiline® cream.

Other methods were also tested which subjected the Raftiline® mixture to a high force of friction, in particular, a household mixer, a homogeniser, a "hydroshear", a colloid mill ultrasonic vibrations, a "microfluidiser" a "rotor-stator" mixer (Silverson, Dispax, Kinematica). By varying the individual parameters of each of the appliances the consistency of the cream changed in the same manner as described in WO 93/06744 (Tiense Suikerraffinaderij, Belgium) with the difference that the consistency of the cream was significantly higher than that which can be obtained using Raftiline® ST, which contains inulin with a native polydispersion (See FIG. 21). High performance Raftiline® cream is also more consistent than Raftiline® LS cream as described in WO 94/12541 (Tiense Suikerraffinaderij, Belgium).

The consistency of a 40% DM Raftiline® LS cream varies between 200 and 240 g as measured using the Stevens LFRA Texture Analyser. The same consistency values have already been achieved with a high performance Raftiline® cream of only 20% DM.

A high performance Raftiline® cream immobilises significantly more water than a cream based on native inulin. A one or two times less amount of high performance Raftiline® is sufficient to produce the same consistency.

A high performance Raftiline® cream has the same fatty texture as Raftiline® ST cream and was used in food products and other products containing oils and fats to wholly or partly replace fats and oils.

The Aw values of a high performance Raftiline® cream at 30% were determined in parallel with Raftiline® ST at 30% with a ROTRONIC Hygroscope BT after leaving 45 minutes or stabilisation: both had the same Aw value of 92.6.

EXAMPLE 10

Solubility in Liquids 1 to 10% solutions of high performance Raftiline® are prepared by dissolving high performance Raftiline® in boiling water. These solutions are left without further mixing. After a number of weeks or months 1 to 3% solutions are still stable. In 4 to 5% solutions a slight precipitation begins to form after 1 or 2 weeks. A 10% solution is stable for only a few hours.

Accordingly high performance Raftiline® can be added to liquids where a heating stage is provided in the method used for preparation.

EXAMPLE 11

Acid Resistance

The process comprises the following steps
Step 1: rapid warming up of a solution adjusted to pH 3 from room temperature to 60° C.;
Step 2: maintain the reaction for one hour at 60° C.;
Step 3: rapid cooling from ⁻60° C. to room temperature and adjusting pH to 3.

The results show that Raftiline® ST hydrolyses almost two times as quick as high performance Raftiline®.

EXAMPLE 12

Crosslinking 20 g of sodium hydroxide is dissolved in 200 ml. of water. After the addition of ice the container is placed in a bed of ice. 120 g of Raftiline® is added while continuously stirring. Once the high performance inulin is suspended, 30 ml of epichlorhydrine is added. After a few days at room temperature there is a firm orange-yellow gel which is pulverised and washed until the wash water is neutral. Acetone is added, which causes a sharp decrease in volume. After drying there is a 153 g quantity of white powder. If Raftiline® ST is used in a similar manner, a brown-yellow to dark brown solution is obtained which after standing for a long time at room temperature evolves into a more viscous solution which does not form a gel. As a consequence, contrary to Raftiline® ST, high performance Raftiline® can be used for netting.

EXAMPLE 13

Acetylation 150 g of high performance Raftiline® is brought into suspension in 500 ml of pyridine with 4 g of dimethylaminopyridine as catalyst. 400 ml of acetic anhydride is added. The reaction mixture is stirred overnight at room temperature and then mixed with 500 ml of dichloromethane. The whole is washed 5 times using 1000 ml washing solution which respectively consists of:
1°) 200 ml methanol/106 g sodium hydroxide/ice water
2°) 100 ml methanol/53 g sodium hydroxide/ice water
3°) 30 g sodium bicarbonate/ice water
4°) 30 g potassium dihydrogen phosphate/ice water
5°) ice water.

The solution washed in this way is colourless and has a yield of 125 g of white powder after dry evaporation.

If Raftiline® ST is used in a similar manner the solution acquires an orange-yellow colour after the preparation of the reaction mixture and turns black within one day (Guiness colour). After washing the end product remains brown. Lyophilisation to produce a powder is not possible, only a very viscous material is obtained.

The brown colouring is an indication for the presence of degradation products consisting or monomers and perhaps reducing oligomers which appear under the basic reaction conditions usual in these chemical modifications. As a consequence of this degradation the yield is significantly lower, and lesser end product is obtained. By the use of high Performance Raftiline®, the brown colouring is significantly less or ceases to occur. High performance Raftiline® therefore lends itself better to chemical modification than native inulin.

EXAMPLE 14

Skimmed Milk with Fibre

| Recipe (% weight): | |
| --- | --- |
| high performance Raftiline ® powder | 1 |
| skimmed milk | 99 |

Method:
Add the high performance Raftiline® gradually to the skimmed milk and stir until the high performance Raftiline® is fully suspended.

Results:
High performance Raftiline® gives a fuller feeling in the mouth to the skimmed milk, but without changing the taste. 1% high performance Raftiline® has the same effect on the mouth as 2% Raftiline® ST. When using whole milk or semi-skimmed milk, a comparable effect is obtained.

EXAMPLE 15

Fat-free Yoghurt

| Recipe (% weight): | |
| --- | --- |
| high performance Raftiline ® cream (25% DM) | 10 |
| skimmed milk | 82 |
| skimmed milk powder | 3 |
| fermenting agent | 5 |

Method:
Prepare the high performance Raftiline® cream and pasteurise it (30 sec, 80° C.).
Mix the skimmed milk and the skimmed milk powder in a container suitable for pasteurisation (add a mix-flea).

Let it settle for 30 minutes.

Pasteurise the solution (5 min, 95° C.).

Cool it down to 45° C. and add the fermenting agent and the Raftiline® cream under sterile conditions.

Stir the mixture with a magnetic stirrer for a few minutes.

Incubate at 42° C. to a pH of 4.7.

Cool down quickly and store at approx. 4° C.

Results:

High performance Raftiline® improves the mouth feeling of fat-free yoghurt. At a dose of 2.5% it produces a fat-free yoghurt with a better and fuller feeling in the mouth than a similar yoghurt with 3.5% Raftiline® ST. High performance Raftiline® can also be added as a powder instead of as a cream. High performance Raftiline® powder can also be used as a replacement for milk powder.

EXAMPLE 16

Fat-free Soft Curd Cheese

| Recipe (weight %): | |
|---|---|
| high performance Raftiline ® cream (20%) | 10 |
| soft curd cheese (0% fat) | 90 |

Methods:

Prepare the high performance Raftiline® cream and pasteurise it (30 sec, 80° C.).

Add this, before it is fully stiffened, to the fat-free soft curd cheese and mix.

Results:

With 2% high performance Raftiline® in the end product the same result is achieved as when using 3.5% Raftiline® ST. The cheese with the high performance Raftiline® has a better feeling in the mouth, is creamier and has more sheen than soft curd cheese without inulin.

A comparable effect is seen when preparing a fat-reduced soft curd cheese of 20% at for example.

EXAMPLE 17

Fat-free Pudding

| Recipe (weight %): | |
|---|---|
| high performance Raftiline ® | 4 |
| skimmed milk powder | 10.1 |
| sucrose | 10 |
| skimmed milk | 74.3 |
| corn starch (Snowflake 06304 Cerestar) | 1.3 |
| gelatine (Aubygel MR 50, Sanofi) | 0.15 |
| vanilla flavouring (209203, Haarmann & Reimer) | 0.1 |
| β-carotene (25142, Universal Flavors) | 0.01 |

Method:

Combine the dry ingredients and mix them into the skimmed milk, together with the flavouring and the colouring.

Heat the mixture to 95° C. for 30 minutes.

Allow to cool.

Results:

High performance Raftiline® contributes to a fat-like feeling in the mouth and an optimum texture. With 4% high performance Raftiline® the same result is achieved as when using 7% Raftiline® ST. High performance Raftiline® can also be used for other desserts such as e.g. chocolate mousse, in which a similar lowering of the Raftiline® content can be achieved in comparison to Raftiline® ST.

EXAMPLE 18

Cream with 24% Fat

| Recipe (weight %) | |
|---|---|
| high performance Raftiline ® | 8 |
| cream (40% fat) | 60 |
| skimmed milk | 32 |

Method:

Heat the skimmed milk to 60° C. and make a cream of this with high performance Raftiline®.

Heat the cream to 40° C. and then mix it with the high performance Raftiline® cream before it is completely stiffened.

Pasteurise the mixture (30 sec, 85° C.).

Allow to cool and store in a cool place.

Results:

This recipe gives the same result as a similar recipe using 14% Raftiline® ST. A cream with only 24% fat cannot be whipped. Thanks to the addition of high performance Raftiline® the cream can be whipped (whipping time and overrun will be similar to those of a standard cream containing 40% fat).

EXAMPLE 19

Cream Cheese with 10% Fat

| Recipe (weight %): | |
|---|---|
| high performance Raftiline ® | 8 |
| ultrafiltration retentate | 75.5 |
| salt | 0.4 | sodium sorbate 0.1 water 16

Method:

Standardise the milk to a fat content of 3.2% and a protein content of 4.0%.

Pasteurise the milk (95° C., 2 minutes).

Homogenise the milk (30 Bar).

Cool off to 22° C. and incubate with starter culture (Flora Danica Normal, Hansens) to a pH of 4.7. Ultrafiltrate at 55° C.

Add the UF retentate and the other ingredients at the same time and mix in a Stephan blender.

Heat for 1 minute to 95° C. and homogenise (two steps, 150 and 50 Bar).

Cool down and store in a cool place.

Results:

High performance Raftiline® heightens the fat-like mouth feeling. This recipe using 8% high performance Raftiline® provides the same texture as a similar recipe using 14% Raftiline® LS. Moreover, the taste obtained using high performance Raftiline® is completely non-sweet. Finally, the product shows more sheen with the use of high performance Raftiline®.

EXAMPLE 20

Cheese Spread with 10% Fat

| Recipe (weight %): | |
| --- | --- |
| high performance Raftiline ® | 6.5 |
| cheddar, 4 months old | 21.5 |
| cheddar, 18 months old | 11.0 |
| disodium phosphate | 0.5 |
| trisodium citrate | 0.2 |
| skimmed milk powder | 2.5 |
| whey powder | 4.3 |
| sodium caseinate | 3.0 |
| whey protein concentrate (75%) | 2.0 |
| water | 48.5 |

Method:

Cut the cheese into pieces and add the water and the other ingredients.

Heat for 2 minutes to 70° C. and blend in a Stephan blender (1500 rpm).

Heat for 1 minute to 80° C. and blend (3000 rpm).

Heat to 85° C. and keep this temperature for 2 minutes and blend (3000 rpm).

Homogenise (two steps, 50 and 150 Bar).

Cool down to 4° C.

Results:

Using 6.5% high performance Raftiline®, a product is achieved that is equivalent to a similar product using 11% Raftiline® LS. Moreover the product shows more of a sheen when using high performance Raftiline®. High performance Raftiline® can also be used in other cheese products, such as fondue cheeses.

EXAMPLE 21

Water-in-oil Bread Spreads (40% Fat)

| Recipe (weight %): | | |
| --- | --- | --- |
| fat phase: | emulsifier (Dimodan OT, Grinsted) | 0.6 |
| | fat and oil blend | 39.4 |
| | β-carotene | 0.02 |
| | flavouring (2934, Grinsted) | 0.02 |
| water phase: | high performance Raftiline ® | 3.0 |
| (pH = 4.7) | water | 56.34 |
| | sodium sorbate | 0.1 |
| | salt | 0.5 |
| | flavouring (2935, Grinsted) | 0.02 |

Method:

Prepare the fat and water phases.

Emulsify these at 50° C.

Put the emulsion through a scraped heat exchanger (A) a kneader (B) and again through a scraped heat exchanger (C).

The temperature of the emulsion after passing through A, B and C respectively should be ±17° C., ±24° C. and ±14° C.

Results:

The product with high performance Raftiline® is comparable to a similar product using 7% Raftiline® LS. Moreover, the product with high performance Raftiline® shows more sheen. high performance Raftiline® can also be used in similar bread spreads which have a different fat content, e.g. 10, 20% or 60%. High performance Raftiline® can likewise be used for oil-in-water spreads with e.g. 0%, 5% or 10% fat. High performance Raftiline® can also be combined with other stabilisers, such as with gelatin, pectin, alginate, carraghenan, caseinate, milk powder or whey powder. For example, 1.5% high performance Raftiline® and 0.6% gelatine in the spread from example 20 is prepared.

EXAMPLE 22

Frankfurter Sausage with 11% Fat

| Recipe (Weight %): | |
| --- | --- |
| high performance Raftiline ® | 5.0 |
| shoulder meat | 39.7 |
| neck bacon | 14.9 |
| ice | 39.6 |
| phosphate | 0.2 |
| nitrated salt | 0.18 |
| ascorbic acid | 0.1 |
| milk proteins | 0.2 |
| herb mix | 0.12 |

Method:

Mince the meat and the bacon.

Add the high performance Raftiline® and mix in some of the water.

Mince further and add the rest of the water plus the remaining ingredients.

Fill up the sausage skins with the mixture.

Heat to 75° C. until a core temperature of 69° C. is reached.

Cool down and store at 4° C.

Results:

The product with 5% high performance Raftiline® is firmer and crisper than a similar product using 7.5% Raftiline® ST. High performance Raftiline® is used in other meat products such as boiling sausage.

EXAMPLE 23

Frankfurter Sausage with 16% Fat

| Recipe (Weight %): | |
| --- | --- |
| lean pork meat | 31.0 |
| back bacon | 8.0 |
| neck bacon | 8.0 |
| high performance Raftiline ® | 5.0 |
| ice | 41.7 |
| milk proteins | 1.9 |
| corn starch | 1.9 |
| nitrated salt | 1.8 |
| herb mix | 0.5 |
| phosphate | 0.2 |

Method:

Mince the pork meat and half of the ice.

Add the salt and the phosphate and mix until it has the expected texture.

Add the back bacon and the neck bacon to the rest of the ice and mix until this too has the expected texture.

Add the milk proteins, the corn starch, the high performance Raftiline 3. and the herb mix and mix it until an homogeneous mixture is obtained.

Fill up the sausage skin with the obtained mixture.

Dry and smoke the Frankfurter& sausage at 50° C. and heat it at 80° C. until a core temperature of 68° C. is reached.

Cool it down under running water, pack it and store them at 4° C.

Results:

According to this recipe, the Frankfurter sausage has a 16% fat content which means a reduction of 40% compared to a full-fat reference recipe.

EXAMPLE 24

Liver Paste

| Recipe (weight %): | |
|---|---|
| pork liver | 40.0 |
| neck bacon | 20.0 |
| rind | 8.0 |
| high performance Raftiline ® | 7.0 |
| water | 17.2 |
| nitrated salt | 1.8 |
| herb mix | 2.0 |
| rice flour | 2.0 |
| milk powder | 2.0 |

Method:

Cook the neck bacon and the rind.

Mince the liver and add slowly the salt to it.

Mince the cooked neck bacon and the rind and add the milk powder to it, the rice flour, the warm water and the high performance Raftiline®.

Mix them all until an homogeneous mass is obtained.

Cool down the temperature to 35° C. and add the liver slowly.

Mince it until the expected texture is obtained.

Add the herb mix and homogenise.

Fill up the paste into pots and close them with a cover.

Heat them at a temperature of 75° C. until a core temperature of 68° C. is obtained.

Cool down the pots and maintain them at a temperature of 4° C.

Results:

According to this recipe, a spreadable liver paste is obtained with a fat content of 13% (weight %) which means a reduction of 60% compared to a standard recipe.

EXAMPLE 25

Fat-free Ice Cream

| Recipe (weight %): | |
|---|---|
| high performance Raftiline ® | 5.0 |
| skimmed milk powder | 11.8 |
| sugar | 12.0 |
| water | 70.3 |
| flavouring (Rhône-Poulenc, David Michaelis Vanilla N & A) | 0.4 |
| stabiliser (Grinsted Cremodan SE 30) | 0.5 |

Method:

Blend the dry products.

Add the water and the flavouring.

Mix for 1 minute.

Pasteurise the solution (80° C., 30 sec).

Cool down the solution to 60° C.

Mix for 1.5 minutes.

Leave overnight (refrigerator).

Make ice cream with the solution in an ice cream machine (Carpigiani, 6.5 minutes).

Results:

In this recipe Raftiline® provides a fat-like feeling in the mouth and 5% of high performance Raftiline® replaces 9% of Raftiline® ST.

EXAMPLE 26

Full Yoghurt

| Recipe (weight %): | | |
|---|---|---|
| | Standard | With high performance Raftiline ® |
| high performance Raftiline ® | — | 2 |
| skimmed milk powder | 2 | — |
| full-cream milk | 94 | 94 |
| fermenting agent | 4 | 4 |

Method:

Blend the skimmed milk and the high performance Raftiline® or the skimmed milk powder in a container suitable for pasteurisation (add a mix-flea).

Let it settle for 30 minutes.

Pasteurise the solution (5 min, 95° C.).

Cool down to 45° C. and add the fermenting agent under sterile conditions. Stir the mixture using a magnetic stirrer for a few minutes.

Incubate at 42° C. to a pH=4.7.

Cool down quickly and store at 4° C.

Results:

High performance Raftiline® gives a similar texture, taste and feeling in the mouth as skimmed milk powder.

EXAMPLE 27

Filling

A) Filling with 80% Dry Material

| Recipe (weight %): | | | | |
|---|---|---|---|---|
| | Filling I | Filling II | Filling III | Filling IV |
| Raftiline ® ST | 18 | / | / | / |
| High performance Raftiline ® | / | 18 | 9 | 12 |
| Sugar S2 | 31 | 31 | 35.5 | 34 |
| Trimoline 80% | 38.8 | 38.8 | 44.4 | 42.5 |
| Water | 12.2 | 12.2 | 11.1 | 11.5 |

Method:

Dissolve the sugars in water heated to approximately 60° C.

Add the Raftiline® while mixing the solution.

Mix uniformly.

Results:

filling I: firm filling, cuts well, short texture filling II: very firm, hard filling, can be cut, short texture filling III: more liquid filling, cannot be cut filling IV: firm filling, cuts well, short texture Used in a filling, Raftiline® forms a cream structure. By replacing Raftiline® ST by high performance Raftiline® the amount of Raftiline® used can be reduced. The level of Raftiline® ST can be reduced from 18% to 12%.

B) Whipped Filling

Recipe (weight %):

| | Filling I | Filling II | Filling III |
|---|---|---|---|
| Powder sugar | 60 | 60 | 66 |
| Water | 15 | 15 | 15 |
| Glycerine | 10 | 10 | 10 |
| Raftiline ® ST | 12 | / | / |
| High performance Raftiline ® | / | 12 | 6 |
| Texture lite | 1 | 1 | 1 |
| Uniguar | 1 | 1 | 1 |
| Vanilla | 0.3 | 0.3 | 0.3 |

Texture lite: emulsifier (Eastman Chemicals)

Uniguar: guar gum (Rhône-Poulenc)

Method:

Weigh the dry ingredients.

Blend in the Kitchen Aid with the blender at position 1.

Heat the water to boiling point and add the glycerine.

Add this mixture to the powders while blending.

Blend for 30 seconds.

Scrape off the sides and beat for 5 minutes at position 6.

Results:

filling I: density: 0.81 g/ml, firm filling filling II density: 0.74 g/ml, very firm filling filling III: density 0.60 g/ml, firm filling, comparable with reference product.

The Raftiline® ST can be replaced by high performance Raftiline®. The amount of high performance Raftiline® is only half the quantity of Raftiline® ST. The filling produced has even better whipping properties. High performance Raftiline® stablizes the whipped structure of a whipped filling.

C) Filling (fourrage) on a Fat Basis

Recipe (weight %):

| Ingredients | Raftiline ® ST | High performance Raftiline ® |
|---|---|---|
| Raftiline ® ST | 47.7 | — |
| high performance Raftiline ® | — | 47.7 |
| cocoa powder | 7.5 | 7.5 |
| skimmed milk powder | 7.5 | 7.5 |
| hazelnut paste | 10 | 10 |
| fat | 26.95 | 26.95 |
| aspartame | 0.15 | 0.15 |
| lecithin | 0.4 | 0.4 |

Results:

High performance Raftiline® may be used in a filling as a substitute of sugar.

Indeed, contrary to a recipe using high performance Raftiline®, one adds 4% of sugars when the Raftiline® ST is used. It is thus possible to obtain a "sugar-free" filling with the use of high performance Raftiline® instead of Raftiline® ST.

EXAMPLE 28

Fibre Enrichment of Baked Goods

Recipe (weight %):

| Ingredients | Raftiline ® ST | High performance Raftiline ® |
|---|---|---|
| Flour | 100 | 100 |
| Eggs | 100 | 100 |
| Shortening | 100 | 100 |
| Raftiline ® ST or high performance Raftiline ® | 25 | 25 |
| Sugar | 75 | 75 |
| V90 | 0.747 | 0.747 |
| BP pyro | 0.083 | 0.083 |

Method:

Allow the fat to soften.

Add the sugar, water and eggs and blend for 1 minute in the Kitchen Aid (pos.1).

Add the sifted flour and the raising agent plus the Raftiline®.

Blend for 3 minutes at position 3.

Place the dough in the baking container and bake for 55 minutes at 210° C.

Results:

Raftiline® can be added as soluble fibre to baked goods, the share of fibre added by high performance Raftiline® is higher compared to the share of fibre added by Raftiline® ST.

The level of fibre in this cake with Raftiline® ST is 7.5%, with high performance Raftiline® this is 8.1%. It may also be used in other products such as biscuits, bread and rusks, and in extruded products.

EXAMPLE 29

Hard Boiled Confectionery

High performance Raftiline® can be added to hard boiled products to increase the viscosity of the melting after cooking.

Method:

Weigh the ingredients into an open saucepan.

Add water and boil to a dry materials level of at least 99%

Pour out onto the cold plate and roll into balls.

Evaluate the viscosity during the processing.

Result:

Evaluation as compared with hard boiled products made with 100% Isomalt:

10% Raftiline® ST the syrup has higher viscosity, stiffens quicker on cooling.

10% High Performance Raftiline®:

syrup has a higher viscosity than with Raftiline® ST.

EXAMPLE 30

Salad Dressing

High performance Raftiline® is used in a salad dressing in the form of a cream.

| Recipe (weight %): | |
|---|---|
| Raftiline ® cream 40% | 65 |
| Water | 22.3 |
| Vinegar | 5.5 |
| Sugar | 2.5 |
| Mustard | 1.5 |
| Salt | 2.5 |
| Sodium sorbate | 0.3 |
| Satiaxiane CX91 | 0.15 |
| Ascorbic acid | 0.08 |
| Flavouring* | 0.05 |
| β-carotene | 0.015 |
| Sorbic acid | 0.1 |

*Flavouring: French Salad Dressing Herbal Flavouring, Quest NN13798

Various Raftiline® creams were used, i.e.

Raftiline® ST cream at 40% as standard;
high performance Raftiline® cream at 40%
high performance Raftiline® cream at 30%
high performance Raftiline® cream at 25%

Method:

Make up a Raftiline® cream.

Blend sugar, salt, S. sorbate, Satiaxane CX91, ascorbic acid and sorbic acid.

Mix for 3 minutes.

Add the flavouring and the Raftiline® cream.

Homogenise in the mixer.

Add mustard, vinegar and β-carotene. Mix the dressing.

Results:

A dressing with 40% high performance Raftiline® cream is much firmer than the standard dressing. A 30% high performance Raftiline® cream is still more firm than the standard product. A dressing with a 25% high performance Raftiline® cream has a texture which is comparable to that of a dressing made with a 40% Raftiline® ST cream.

EXAMPLE 31

Chocolate

| Ingredients | Recipe (weight %): Raftiline ® ST | High performance Raftiline ® |
|---|---|---|
| Raftiline ® ST | 43.6 | — |
| high performance Raftiline ® | — | 43.6 |
| cocoa mass | 7.5 | 7.5 |
| skimmed milk powder | 19 | 19 |
| hazelnut paste | 2.7 | 2.7 |
| cocoa butter | 19 | 19 |
| butter fat | 3.7 | 3.7 |
| vanilla | 0.03 | 0.03 |
| aspartame | 0.08 | 0.08 |
| lecithin | 0.5 | 0.5 |

Results:

Sugar is replaced by Raftiline®. The chocolate produced has a lower calorific value and contains less added sugar. Through the use of high performance Raftiline® the chocolate can be made without added sugar.

EXAMPLE 32

Chewing Gum

| Ingredients | Recipe (weight %): Raftiline ® ST | High performance Raftiline ® |
|---|---|---|
| Raftiline ® ST | 28.3 | — |
| high performance Raftiline ® | — | 28.3 |
| gum base | 24 | 24 |
| lycasine | 22.6 | 22.6 |
| polyol | 24.49 | 24.49 |
| mint flavour | 0.03 | 0.03 |
| aspartame | 0.08 | 0.08 |
| glycerine | 0.5 | 0.5 |

Results:

Raftiline® can be used in chewing gum in the mass, the powder casing and in the hard coating around chewing gum.

The chewing gum using high performance Raftiline® instead of Raftiline® ST is a chewing gum without added sugar.

EXAMPLE 33

Hamburger

| Recipe (weight %): | |
|---|---|
| lean beef | 48.00 |
| beef | 20.50 |
| Raftiline ® cream | 30.00 |
| herbs | 1.5 |

Raftiline® creams containing 50% Raftiline® ST and 25% high performance Raftiline® respectively were used.

Method:

Chop the lean beef and the beef, blend and add the herbs.

Add the Raftiline® cream.

Form the pieces of meat and store under refrigeration.

Results:

The hamburger with 25% high performance Raftiline® has the same structure and feeling in the mouth as the hamburger with 50% Raftiline® ST.

In a hamburger, 30% of the meat may be replaced by high performance Raftiline®, and this provides an enrichment of fibre content, a reduction of the energy value and a reduction in price, without changing the taste or the texture.

EXAMPLE 34

Chocolate Mousse

| Recipe (weight %): | |
|---|---|
| high performance Raftiline ® | 1.5 |
| skimmed milk powder | 7.0 |
| skimmed milk | 67.4 |
| sugar | 17.5 |
| cocoa powder | 4.0 |
| Filgel (Quest Int. 9323) | 2.1 |
| gelatine (Sanofi B.I. 80 Bls) | 0.5 |

Method:
 Dissolve the sugar, the gelatine and the emulsifier into the milk.
 Heat the whole to 65° C. in a hot water bath.
 Add the rest of the ingredients while stirring the mixture slowly. Homogenise the mixture (150 Bar).
 Pasteurise the mixture at 90° C. and cool down rapidly to a temperature below 20° C.
 Lighten the mixture with air in a Hobart Kitchen Aid for 15 minutes and pour into a container.
 Store in a cool place.

EXAMPLE 35

Salad Dressing (20%fat) Using Powder

| Recipe (weight %): | |
| --- | --- |
| high performance Raftiline ® powder | 3.0 |
| corn oil | 20.0 |
| water | 54.7 |
| vinegar | 7.0 |
| eggs | 5.0 |
| starch (National Starch therm-flo) | 4.0 |
| sugar | 3.0 |
| mustard | 1.5 |
| salt | 1.5 |
| sodium sorbate | 0.05 |
| flavouring (Givaudan Roure 86980-DO) | 0.25 |

Method
 Add starch, sodium sorbate and high performance Raftiline® to the water and blend until a uniform mixture is achieved.
 Add sugar, vinegar and salt and blend well.
 Heat the mixture to 85° C. while continually stirring.
 Cool down to 38° C.
 Add the eggs and beat the mixture for 90 seconds.
 Add the mustard and the flavouring and blend.
 Add the oil while continually stirring.
 Pour into jars and store in a cool place.
 High performance Raftiline® can also be used in the powder form for the preparation of salad dressing.

EXAMPLE 36

Stability of High Performance Raftiline® in Salad-Dressing

| | Recipe (weight %): | | | |
| --- | --- | --- | --- | --- |
| Ingredient | Reference | 1 | 2 | 3 |
| High performance Raftiline ® powder | | 3.00 | | |
| High performance Raftiline ® cream 25% | | | 12.00 | |
| Raftiline ® ST powder | | | | 6.00 |
| Corn oil | 20.00 | 20.00 | 20.00 | 20.00 |
| Water | 57.70 | 54.70 | 45.70 | 51.70 |
| Vinegar | 7.00 | 7.00 | 7.00 | 7.00 |
| Eggs | 5.00 | 5.00 | 5.00 | 5.00 |
| Starch * | 4.00 | 4.00 | 4.00 | 4.00 |
| Sugar | 3.00 | 3.00 | 3.00 | 3.00 |
| Mustard | 1.50 | 1.50 | 1.50 | 1.50 |
| Salt | 1.50 | 1.50 | 1.50 | 1.50 |
| Calcium sorbate | 0.05 | 0.05 | 0.05 | 0.05 |
| Flavouring ** | 0.25 | 0.25 | 0.25 | 0.25 |

* National starch: Therm-Flo
** Givaudan Roure 86980-D0

Method:
 Add starch, calcium sorbate and high performance Raftiline® powder (recipe 1) or Raftiline® ST (recipe 3) to the water and mix it until becomes homogeneous.
 Add the sugar, vinegar and salt and mix it well.
 Heat up the mixture to 85° C. under continuous stirring.
 Cool down to 75° C. and add to it the high performance Raftiline cream® (recipe 2).
 Cool down further to 38° C.
 Add the eggs and shake up the mixture for 90 seconds.
 Add the mustard and the flavouring and mix.
 Add the oil under continuous mixing conserve.
Stability:
 break-down: HPLC enzymatic hydrolysis
 viscosity: Brookefield helipath at 25° C.
 hardness:
  Stevens Texture Analyser
  last peak, penetration depth=25 mm
  penetration speed=0.2 mm/s
Preservation reference salad-dressing:

| | Viscosity (cps) | | Hardness (g) | |
| --- | --- | --- | --- | --- |
| | Room temp | 5° C. | Room temp | 5° C. |
| 1 night | 14885 | 15626 | 40 | 52 |
| 1 week | 14046 | 14540 | 40 | 51 |
| 2 weeks | 13559 | 13078 | 45 | 57 |
| 1 month | 14420 | 13537 | 53 | 62 |
| 2 months | 14264 | 12313 | 40 | 62 |
| 4 months | 15819 | 10836 | 39 | 52 |
| 6 months | 13104 | 14001 | 34 | 48 |
| 9 months | 22893 | 13260 | 47 | 42 |

Preservation Salad-dressing with 3% High Performance Raftiline®:

| | Break down | | Viscosity (cps) | | Hardness (g) | |
| --- | --- | --- | --- | --- | --- | --- |
| | Room temp | 5° C. | Room temp | 5° C. | Room temp | 5° C. |
| 1 night | 0 | 0 | 14079 | 16380 | 40 | 83 |
| 1 week | 0 | 0 | 18531 | 18648 | 50 | 69 |
| 2 weeks | 0 | 0 | 26325 | 28821 | 67 | 84 |
| 1 month | 0 | 0 | 33540 | 32318 | 76 | 93 |
| 2 months | 0 | 0 | 168450 | 163800 | 65 | 82 |
| 4 months | 0 | 0 | 191613 | 153326 | 71 | 93 |
| 6 months | 9.4 | 0 | 197340 | 167817 | 63 | 84 |
| 9 months | 34.4 | 15.6 | 223704 | 162552 | 83 | 91 |

Preservation Salad-dressing with 6% Raftiline® ST:

|  | Break down | | Viscosity (cps) | | Hardness (g) | |
| --- | --- | --- | --- | --- | --- | --- |
|  | Room temp | 5° C. | Room temp | 5° C. | Room temp | 5° C. |
| 1 night | 0 | 0 | 16926 | 17394 | 45 | 55 |
| 1 week | 1.8 | 0 | 30203 | 26130 | 46 | 56 |
| 1 month | 5.4 | 3.6 | 463320 | 408720 | 77 | 87 |
| 2 months | 8.9 | 1.8 | 440115 | 348075 | 73 | 80 |
| 4 months | 16.1 | 8.9 | 481455 | 376155 | 73 | 81 |
| 6 months |  |  | 691080 | 363000 | 79 | 83 |

Results:
Adding high performance Raftiline® or Raftiline® ST in powder or in cream form gives an improvement of mouth feeling. Though the concentration of high performance Raftiline® can be reduced compared to Raftiline® ST, the same mouth feeling is obtained.

The salad-dressing obtained with high performance Raftiline® is more resistant to hydrolysis than the salad-dressing obtained with Raftiline® ST.

EXAMPLE 37

Instant Bechamel Sauce

| Recipe (weight %): | |
| --- | --- |
| high performance Raftiline ® powder | 1.50 |
| flour | 1.75 |
| modified starch (Cerestar C Top 12616) | 3.50 |
| caseinate | 1.0 |
| Carrageenan (Sanofi B.I. Gelogen 4M) | 0.18 |
| pepper | 0.01 |
| salt | 0.50 |
| onion | 0.15 |
| Nutmeg | 0.03 |
| skimmed milk | 91.38 |

Method:
Blend together all dry ingredients.
Dissolve the dry mixture in the milk while continually stirring.
Heat up the mixture to produce an instant sauce.

Results:
Without any problem, high performance Raftiline® powder can be added to instant powder mixtures and will not lead to lump-forming.

EXAMPLE 38

Gouda Cheese

| Recipe (weight %): | |
| --- | --- |
| full-cream milk | 47.1 |
| skimmed milk | 47.1 |
| high performance Raftiline ® | 5.00 |
| β-carotene | q.s. |
| rennet | q.s |
| starter culture | 0.8 |
| calcium chloride | 0.02 |
| sodium nitrate | 0.005 |

Method:
Blend the full-cream and skimmed milk to produce a fat content of 1.5%.
Add high performance Raftiline® and mix until a uniform mixture is achieved.
Pasteurise the milk at 75° C. for 20 seconds.
Cool down to 30° C.
Add the β-carotene, rennet, starter culture, calcium chloride and sodium nitrate.
Allow the rennet to work for a minimum of 30 minutes at 30° C. and then allow the first whey to run off.
Wash the curd with water and stir.
Remove the second whey.
Press together, salt and allow to mature for four or more weeks.

Results:
With the use of high performance Raftiline® a good deal less inulin is lost via the whey and 30 to 40% can be retained. A Gouda cheese with a better texture is obtained in the final product. It is more creamy, less chewy or rubbery. The yield of cheese preparation is enhanced.

EXAMPLE 39

Daytime Skin-care Cream (O/W)

| Recipe (weight %): | |
| --- | --- |
| A. high performance Raftiline ® | 3.0 |
| decyloleate | 10.0 |
| liquid paraffin | 3.0 |
| stearic acid | 8.0 |
| dimethicone | 1.0 |
| Vitamin E acetate | 0.5 |
| B. carbomere 940 | 0.3 |
| aqua conservans | to 100 |
| diluted sodium hydroxide | to pH = 6.5 |

Method:
Scatter the carbomere on the water and allow to stand for 1 day.
Prepare A at 70° C.
Heat B to 70° C.
Add A and B together at 70° C. and stir.
Neutralise with the diluted sodium hydroxide to a pH approximately equal to 6.5.
Raftiline® can also be used to replace the carbomere as a consistency provider.

What is claimed is:

1. A fractionated chicory inulin composition, consisting essentially of a crystallized fractionated polydisperse chicory inulin composition which:
   (A) is in the form of spherical particles that have a diameter comprised between 1 and 100 μm, and that present radial symmetry, double breaking and perpendicular fade cross under polarised light;
   (B) has an average degree of polymerisation (av. DP) between 20 and 40;
   (C) contains less than 0.2 wt % of monomers and less than 0.2 wt % of dimers and less than 1.5 wt % of oligomers with a DP<10;
   (D) contains less than 0.2 wt % ash; and
   (E) contains no detectable amount of alcohol.

2. The composition according to claim 1, wherein the spherical particles have a diameter comprised between 5 and 70 μm.

3. The composition according to claim 1 in spray-dried form.

4. The composition according to claim 2 in spray-dried form.

5. The composition according to claim 1 wherein the inulin composition is esterified, etherified, oxidized and/or cross-linked.

6. A composition having a creamy structure comprising the inulin composition according to claim 1.

7. A composition having a creamy structure comprising the inulin composition according to claim 2.

8. A pelletized composition including the composition according to claim 3 which forms instantly a colloidal dispersion.

9. A pharmaceutical, cosmetic, feed and/or food composition comprising the composition according to claim 1.

10. A pharmaceutical, cosmetic, feed and/or food composition comprising the composition according to claim 3.

11. A process for producing a crystallized fractionated polydisperse chicory inulin composition from a native polydisperse chicory inulin by a directed crystallization of an inulin solution, which comprises the steps in sequence of:
  (A) a rapid achievement of a high degree of super saturation obtained by bringing a native polydisperse chicory inulin into solution in water solvent at a temperature above 85° C. and by a rapid cooling by a heat exchanger to a temperature between −6° C. and 40° C. at a rate between 0.2° C./sec and 10° C./sec, or by a rapid concentration increase through evaporation of the solvent, or by a combination thereof, to provide said crystallized fractionated polydisperse inulin in the form of particles;
  (B) separation of the particles after crystallization from the obtained suspension; and
  (C) washing the separated particles with water, yielding a crystallized fractionated chicory inulin composition that;
    (i) is in the form of spherical particles that have a diameter comprised between 1 and 100 μm, and that present radial symmetry, double breaking and perpendicular fade cross under polarised light;
    (ii) has an average degree of polymerisation (av. DP) which is double or higher than an av. DP of the native polydisperse inulin composition;
    (iii) contains less than 0.2 wt % of monomers and less than 0.2 wt % of dimers and less than 1.5 wt % of oligomers with a DP<10;
    (iv) contains less than 0.2 wt % ash; and
    (v) contains no detectable amount of alcohol.

12. The process according to claim 11, wherein the particles separated after crystallization are washed with demineralized water at 15° C.

13. The process according to claim 11, wherein grafting particles are used in the directed crystallization.

14. The process according to claim 11, wherein the process further comprises the step of drying of the washed particles.

15. The process according to claim 11, wherein the process further comprises the step of drying of the washed particles by spray-drying.

16. The process according to claim 13, wherein the process further comprises the step of drying of the washed particles.

17. The process according to claim 13, wherein the process further comprises the step of drying of the washed particles by spray-drying.

18. The process according to claim 11, wherein the process further comprises the step of chemical or enzymatic modification of the washed particles.

19. The process according to claim 11, wherein step (A) comprises:
  a directed crystallization comprising a rapid achievement of a high degree of super saturation obtained by bringing native chicory inulin into solution in water at a concentration between 15 and 60% dry mass at a temperature above 85° C., and rapid cooling at a cooling rate between 1° C./sec and 7° C./sec to a temperature between 15° C. and 25° C., including the use of grafting particles in a ratio to the particles to be produced of 1/100 to 1/200,000 (expressed as wt %), providing crystallized fractionated polydisperse chicory inulin in the form of particles; and
  step (C) comprises washing of the separated particles with demineralized water at 15° C., whereby the resulting crystallized fractionated chicory inulin composition
    (i) is in the form of spherical particles that have a diameter comprised between 1 and 100 μm, and that present radial symmetry, double breaking and perpendicular fade cross wider polarised light;
    (ii) has an average degree of polymerisation (av. DP) between 20 and 40;
    (iii) contains less than 0.2 wt % of monomers and less than 0.2 wt % of dimers and less than 1.5 wt % of oligomers with a DP<10;
    (iv) contains less than 0.2 wt % ash; and
    (v) contains no detectable amount of alcohol.

20. The process according to claim 19, wherein said grafting particles are used in a ratio to the particles to be produced of 1/5,000 to 1/80,000 (expressed as wt %), yielding said crystallized fractionated polydisperse chicory inulin in the form of spherical particles that have a diameter comprised between 5 to 70 μm.

21. The process according to claim 19, furthermore comprising drying of the washed particles.

22. The process according to claim 19, furthermore comprising drying of the washed particles by spray-drying.

23. The process according to claim 20, furthermore comprising drying of the washed particles.

24. The process according to claim 20, furthermore comprising drying of the washed particles by spray-drying.

25. The process according to claim 19, furthermore comprising the step of chemical or enzymatic modification of the washed particles.

* * * * *